US007189865B2

(12) United States Patent
Ternansky et al.

(10) Patent No.: US 7,189,865 B2
(45) Date of Patent: Mar. 13, 2007

(54) THIOMOLYBDATE ANALOGUES AND USES THEREOF

(75) Inventors: Robert J. Ternansky, San Diego, CA (US); Andrew Mazar, San Diego, CA (US); Patricia L. Gladstone, San Diego, CA (US); Dimitri Coucouvanis, Ann Arbor, MI (US); Amy L. Allan, Encinitas, CA (US); Sean M. O'Hare, San Diego, CA (US); Melissa L. P. Price, Cardiff, CA (US); Steven Robert Pirie-Shepherd, Cardiff, CA (US); Fernando Donate, San Diego, CA (US)

(73) Assignees: Attenuon, LLC, San Diego, CA (US); Regents of the University of Michigan, Ann Arbor, MI (US)

( * ) Notice: Subject to any disclaimer, the term of this patent is extended or adjusted under 35 U.S.C. 154(b) by 194 days.

(21) Appl. No.: 10/447,585

(22) Filed: May 28, 2003

(65) Prior Publication Data

US 2004/0019087 A1   Jan. 29, 2004

Related U.S. Application Data

(63) Continuation-in-part of application No. 10/436,958, filed on May 12, 2003, now abandoned, which is a continuation-in-part of application No. 10/202,346, filed on Jul. 23, 2002, now abandoned.

(60) Provisional application No. 60/434,742, filed on Dec. 18, 2002.

(51) Int. Cl.
*C07F 11/00* (2006.01)
*A61K 31/28* (2006.01)
*A61K 31/14* (2006.01)

(52) U.S. Cl. .................. 556/57; 564/295; 514/492; 514/642

(58) Field of Classification Search .................. 556/57; 564/295; 514/492, 642
See application file for complete search history.

(56) References Cited

U.S. PATENT DOCUMENTS

| | | | |
|---|---|---|---|
| 2,909,541 | A | 10/1959 | Hugel |
| 3,845,770 | A | 11/1974 | Theeuwes et al. |
| 3,916,899 | A | 11/1975 | Theeuwes et al. |
| 4,343,746 | A | 8/1982 | Anglin et al. |
| 4,765,539 | A | 8/1988 | Noakes et al. |
| 5,112,598 | A | 5/1992 | Biesalski |
| 5,556,611 | A | 9/1996 | Biesalski |
| 5,639,725 | A | 6/1997 | O'Reilly et al. |
| 5,698,155 | A | 12/1997 | Grosswald et al. |
| 5,950,619 | A | 9/1999 | van der Linden et al. |
| 5,954,047 | A | 9/1999 | Armer et al. |
| 5,970,974 | A | 10/1999 | van der Linden et al. |

FOREIGN PATENT DOCUMENTS

WO   WO 99/20374 A1   4/1999

OTHER PUBLICATIONS

Alonso et al., Inorganica Chimica Acta (2001), 325, p. 193-197.*
Bajou et al., "Absence of Host Plasminogen Activator Inhibitor 1 Prevents Cancer Invasion and Vascularization," *Nat. Med.* (1998), 4:923-928.
Bamba et al., "Release Mechanisms in Gelforming Sustained Release Preparations," *Int. J. Pharm.* (1979) 2:307.
Benjamin et al., "Selective Ablation of Immature Blood Vessels in Established Human Tumors Follows Vascular Endothelial Growth Factor Withdrawal," *J. Clin. Invest.* (1999), 103: 159-165.
Blood et al., "Tumor Interactions With the Vasculature: Angiogenesis and Tumor Metastasis" *Biochim. Biophys. Acta* (1990), 1032:89-118.
Borgstrom et al., "Neutralizing Anti-Vascular Endothelial Growth Factor Antibody Completely Inhibits Angiogenesis and Growth of Human Prostate Carcinoma Micro Tumors in Vito," *Prostrate* (1998), 35:1-10.
Brem et al., "Inhibition of Angiogenesis and Tumor Growth in the Brain," *Am. J. Pathol.* (1990), 137(5): 1121-1142.
Brem et al., "Anti Copper Treatment Inhibits Pseudopodial Protrusion and the Invasive Spread of 9L Gliosarcoma Cells in the Rat Brain," *Neurosurgery* (1990), 26:391-396.
Brown, "Metal Toxicity and Therapeutic Intervention," *Biochem. Soc. Trans* (2002), 30:742-745.
Brown, "Copper and Prion Disease," *Brain Res. Bull.* (2001), 55:165-173.
Carri et al., "Copper-Dependent Oxidative Stress, Alteration of Signal Transduction and Neurodegeneration in Amyothophic Lateral Sclerosis," *Funct. Neurol* (2001), 16:181-188.
Chakravarty et al., "Serum Copper in Malignant Neoplasia with Special Reference to the Cervix Uteri," *J Cancer Res. Clin. Oncol.* (1984), 108: 312-315.
Chambers et al., "Macrophage Colony-stimulating Factor Mediates Invasion of Ovarian Cancer Cells through Urokinase," *Canc. Res.* (1995), 55:1578-1585.
Chen et al., "TNF-R1 Signaling: A Beautiful Pathway," *Science* (2002), 296:1634-1635.
Crowley et al., "Prevention of Metastasis by Inhibition of the Urokinase Receptor," *Proc. Natl. Acad. Sci. USA* (1993), 90:5021-5025.
During et al., "Controlled Release of Dopamine from a Polymeric Brain Implant; In Vivo Characterization," *Ann. Neurol.* (1989) 25:351-356.

(Continued)

*Primary Examiner*—Brian Davis
(74) *Attorney, Agent, or Firm*—Jones Day

(57) ABSTRACT

The current invention provides novel thiomolybdate derivatives, methods of making novel thiomolybdate derivatives, pharmaceutical compositions of novel thiomolybdate derivatives, methods of using novel thiomolybdate derivatives to treat diseases associated with aberrant vascularization, copper metabolism disorders, neurodegenerative disorders, obesity or NF-κB dysregulation and methods of using pharmaceutical compositions of thiomolybdate derivatives to treat diseases associated with aberrant vascularization, copper metabolism disorders, neurodegenerative disorders, obesity or NF-κB dysregulation.

112 Claims, 6 Drawing Sheets

OTHER PUBLICATIONS

Folkman, "Anti-Angiogenesis: New Concept for Therapy of Solid Tumors," *Ann. Surg.* (1972), 175: 409-416.

Folkman, "The Influence of Angiogenesis Research on Management of Patients with Breast Cancer," *Breast Cancer Res. Treat* (1995), 36(2): 109-118.

Folkman, "Angiogenesis Inhibitors Generated by Tumors," *Mol. Med.* (1995), 1(2): 120-122.

Gnjec et al., "Transition Metal Chelator Therapy—A potential Treatment For Alzheimer's Disease?" *Front Biosci.* (2002), 16-23.

Goodson, "Medical Applications of Controlled Release" (1984), 2: 115-138.

Gorelik et al., "Control of Lung Metastasis Progression in Mice: Role of Growth Kinetics of 3LL Lewis Lung Carcinoma and Host Immune Reactivity," *J. Nat'l. Canc. Inst.* (1980), 65:1257-1264.

Gorelik, et al., "Host's Immune State and Kinetics of Local Tumor Growth Control—Progression of Postoperative Lung Metastasis," *Rec. Results Canc. Res.* (1980), 75:20-28.

Gullino, "Considerations on the Mechanism of the Angiogenic Response," *Anticancer Res.* (1986), 6:153-158.

Hanada, et al., "Regulation of Cytokine Signaling and Inflammation," *Cytokine Growth Factor Rev.* (2002), 13: 413-421.

Hanahan et al., "Patterns and Emerging Mechanisms of the Angiogenic Switch During Tumorigenesis," *Cell* (1996), 86(3): 353-364.

Hilgard et al., "Oral Anticoagulation in the Treatment of a Spontaneously Metastasising Murine Tumor (3LL)," *Br. J. Cancer* (1977), 35:78-86.

Howard et al., "Intracerebral drug delivery in rats with lesion-induced memory deficits," *J. Neurosurg.* (1989) 71:105-112.

Isakov et al., "An Immune Response Against the Alloantigens of the 3LL Lewis Lung Carcinoma Prevents the Growth of Lung Metastases, but Not of Local Allografts," *Invasion Metas.* (1982), 2:12-32.

Kleinman et al., "Basement Membrane Complexes with Biological Activity," *Biochemistry* (1986), 25: 312-318.

Koch et al., "Interleukin-8 as a Macrophage-Derived Mediator of Angiogenesis," *Science* (1992), 258:1798-1801.

Kowalik-Jankowska et al., "Possible Involvement of Copper (II) in Alzheimer Disease," *Environ Health Perspect.* (2002), 5: 869-870.

Langer et al., "Chemical and Physical Structure of Polymers as Carriers for Controlled Release of Bioactive Agents: A Review," *J Macromol. Sci. Rev. Macromol Chem.* (1983) 23:61-126.

Langer, "New Methods of Drug Delivery," *Science* (1990) 249: 1527-1533.

Levy et al., Inhibition of Calcification of Bioprosthetic Heart Valves by Local Controlled-Release Diphosphonate, *Science* (1985) 228: 190-2.

Llanos et al., "The Molecular Basis of Copper Homeostasis and Copper-Related Disorders," *DNA Cell Biol..* (2002), 21: 259-270.

Loskutoff et al., "A Powerful Genetic Model to Study Hemostatic Gene Expression in Obesity/NIDDM," *Ann. N.Y. Acad. Sci.* (2000), 902:272-282.

Malave et al., "Influence of Inoculation Site on Development of the Lewis Lung Carcinoma and Suppressor Cell Activity in Syngeneic Mice," *J. Nat'l. Canc. Inst.* (1979), 62:83-88.

Mandinov, et al., "Copper Chelation Represses the Vascular Response To Injury" *PNAS* (2003), 100:6700-6705.

Maynard et al., "Overexpression of Alzheimer's Disease Amyloid-β Opposes the Age-dependent Elevations of Brain Copper and Iron," *J. Biol. Chem.* (2002), 277(47):44670-44676.

Merajver et al., "Copper depletion as an anti-angiogenic strategy in HER2-neu transgenic mice," *Proceedings of Special AACR Conference on Angiogenesis and Cancer*, Abstract #B-11, Jan. 22-24, (1998).

Millauer et al., "Dominant-Negative Inhibition of Flk-1 Suppresses the Growth of Many Tumor Types in *Vivo,*" *Cancer Res.* (1996), 56:1615-1620.

Min et al., "Urokinase Receptor Antagonists Inhibit Angiogenesis and Primary Tumor Growth in Syngeneic Mice," *Cancer Res.* (1996) 56: 2428-2433.

Miyake et al., "Transforming Growth Factor-β1 Stimulates Contraction of Human Glioblastoma Cell-Mediated Collagen Lattice through Enhanced α2 Integrin Expression," *J. Neuropathol. Exp. Neurol.* (2000), 59:18-28.

Nguyen et al., "Quantitation of Angiogenesis and Antiangiogenesis in the Chick Embryo Chorioallantoic Membrane," *Microvascular Res.* (1994), 47:31-40.

Odedra et al., "Low Molecular Weight Angiogenesis Factors," *Pharmac. Ther.* (1991), 49:111-124.

Osawa et al., "Tumor Necrosis Factor Alpha-Induced Interleukin-8 Production via NF-κB and Phosphatidylinositol 3-Kinase/Akt Pathways Inhibits Cell Apoptosis in Human Hepatocytes," *Infect. Immun.* (2002), 70:6294-6301.

Pan et al., "Copper Deficiency Induced by Tetrathiomolybdate Suppresses Tumor growth and Angiogenesis," *Cancer Res.* (2002), 62: 4854-4859.

Parish et al., "A Basement-Membrane Permeability Assay Which Correlates with the Metastatic Potential of Tumor Cells," *Int. J. Cancer* (1992), 52:378-383.

Parke et al., "Characterization and Quantification of Copper Sulfate-Induced Vascularization of the Rabbit Cornea" *Am. J. Pathol.* (1988), 130:173-178.

Passaniti et al., "A Simple, Quantitative Method for Assessing Angiogenesis and Antiangiogenic Agents using Reconstituted Basement Membrane, Heparin, and Fibroblast Growth Factor," *Lab Invest.* (1992), 67:519-528.

Patstone et al., "Copper and Calcium Binding Motifs in the Extracellular Domains of Fibroblast Growth Factor Receptors," *J Biol. Chem.* (1996), 271(7):3343-3346.

Perry et al., "The Role of Iron and Copper in the Aetiology of Neurodegenerative Disorders," *CNS Drugs* (2002), 16:339-352.

Rabbani et al., "Prevention of Prostate-Cancer Metastasis *In Vivo* By a novel Synthetic Inhibitor of Urokinase-Type Plasminogen Activator (uPA)," *Int. J. Cancer* (1995), 63: 840-845.

Raju et al., "Ceruloplasmin, Copper Ions, and Angiogenesis," *Natl. Cancer Inst.* (1982), 69:1183-1188.

Redman et al., "Phase II Trial of Tetrathiomolybdate in Patients with Advanced Kidney Cancer," *Clinical Cancer Research* (1966) 9:1666-1672.

Rupnick et al., "Adipose Tissue Mass Can Be Regulated Through the Vasculature," *Proc. Natl. Acad. Sci.* (2002), 99:10730-10735.

Saudek et al., "A preliminary trial of the programmable implantable medication system for insulin delivery," *N. Engl. J. Med.* 321:574, (1989).

Schnaper et al., "Plasminogen Activators Augment Endothelial Cell Organization In Vitro by Two Distinct Pathways," *J. Cell. Physiol.* (1995), 165:107-118.

Sefton "Implantable pumps," (1987) *CRC Crit. Rev Biomed. Eng* 14(3): 201-240.

Sen, et al. "Copper-Induced Vascular Endothelial Growth Factor Expression and Wound Healing," *Am. J. Physiol Heart Circ Physiol* (2002) 282:H1821-H1827.

Shockley et al., "Penetration of Tumor Tissue by Antibodies and Other Immunoproteins," *Ann. N.Y. Acad. Sci.* (1991), 617: 367-382.

Strausak et al., "Copper in Disorders with Neurological Symptoms: Alzheimer's, Menkes, and Wilson diseases," *Brain Res. Bull.* (2001), 55: 175-185.

Talmadge et al., "Enhanced Metastatic Potential of Tumor Cells Harvested From Spontaneous Metastases of Heterogeneous Murine Tumors," *J. Nat'l. Canc. Inst.* (1982),69:975-980.

Thakur et al., "Indium-111-Labeled Leukocytes for the Localization of Abscesses: Preparation, Analysis, Tissue Distribution, and Comparison with Gallium-67 Citrate in Dogs," *J. Lab. Clin. Med.* (1977), 89:217-228.

Treat et al., in "Liposomes in the Therapy of Infectious Disease and Cancer," Lopez-Berestein and Fidler (eds.), Liss, New York, (1989) 353-365.

Van Golen et al., "Suppression of Tumor Recurrence and Metastasis by a Combination of the PHSCN Sequence and the Antiangiogenic Compound Tetrathiomolybdate in Prostate Carcinoma," *Neoplasia* 4(5):373-379 (2002).

Verma et al., "Osmotically Controlled Oral Drug Delivery," *Drug Develop. Indus. Pharm.* (2000), 26(7): 695-708.

Verschoyle et al., "Pharmacokinetics of Isotretinoin (ISO) in Rats Following Oral Dosing or Aerosol Inhalation," *British J. Cancer* (1999), 80, Suppl. 2, 96.

Volpert et al., "Captopril Inhibits Angiogenesis and Slows the Growth of Experimental Tumors in Rats," *J. Clin. Invest.* (1996), 98:671-679.

Xing et al., "Overexpression of Urokinase Receptor in Breast Cancer Cells Results in Increased Tumor Invasion, Growth and Metastasis," *Int. J. Cancer* (1996), 67:423-429.

Yoshida et al., "Copper Chelation Inhibits Tumor Angiogenesis in the Experimental 9L: Gliosarcoma Model," *Neurosurgery* (1995), 37(2): 287-295.

Ziche et al., "Role of Prostaglandin $E_1$ and Copper in Angiogenesis," *Natl. Cancer Inst.* (1982), 69: 475-482.

* cited by examiner

THIOMOLYBDATE ANALOGUES AND USES THEREOF

This application is a Continuation-In-Part of U.S. patent application Ser. No. 10/436,958, filed May 12, 2003 now abandoned, which is a CIP of U.S. patent application Ser. No. 10/202,346, filed Jul. 23, 2002 now abandoned, and claims benefit of Provisional Application Ser. No. 60/434,742, filed Dec. 18, 2002. The entire contents of the above applications are herein incorporated by reference, in their entirety.

1. FIELD OF THE INVENTION

The present invention relates generally to new thiomolybdate derivatives, methods of making novel thiomolybdate derivatives, pharmaceutical compositions of novel thiomolybdate derivatives, methods of using novel thiomolybdate derivatives and pharmaceutical compositions of novel thiomolybdate derivatives to treat or prevent diseases associated with aberrant vascularization, copper metabolism disorders, neurodegenerative disorders, obesity or NF-κB dysregulation.

2. BACKGROUND OF THE INVENTION

Most forms of cancer are derived from solid tumors (Shockley et al., *Ann. N.Y. Acad. Sci.* 1991, 617: 367–382), which have proven resistant in the clinic to therapies such as the use of monoclonal antibodies and immunotoxins. Anti-angiogenic therapy for the treatment of cancer was developed from the recognition that solid tumors require angiogenesis (i.e., new blood vessel formation) for sustained growth (Folkman, *Ann. Surg.* 1972, 175: 409–416; Folkman, *Mol. Med.* 1995, 1(2): 120–122; Folkman, *Breast Cancer Res. Treat.* 1995, 36(2): 109–118; Hanahan et al., *Cell* 1996, 86(3): 353–364). Efficacy of anti-angiogenic therapy in animal models has been demonstrated (Millauer et al., *Cancer Res.* 1996, 56:1615–1620; Borgstrom et al., *Prostrate* 1998, 35:1–10; Benjamin et al., *J. Clin. Invest.* 1999, 103: 159–165; Merajver et al., *Proceedings of Special AACR Conference on Angiogenesis and Cancer* 1998, Abstract #B-11, January 22–24). In the absence of angiogenesis, internal cell layers of solid tumors are inadequately nourished. Further, angiogenesis (i.e., aberrant vascularization) has been implicated in numerous other diseases (e.g., ocular neovascular disease, macular degeneration, rheumatoid arthritis, etc.). More recently, angiogenesis inhibition has been directly correlated with adipose tissue loss and weight loss in animal models, which suggests anti-angiogenic therapy may be useful in prevention of obesity (Rupnick et al., *Proc. Natl. Acad. Sci.* 2002, 99:10730–10735).

Contrastingly, normal tissue does not require angiogenesis except under specialized circumstances (e.g., wound repair, proliferation of the internal lining of the uterus during the menstrual cycle, etc.). Accordingly, a requirement for angiogenesis is a significant difference between tumor cells and normal tissue. Importantly, the dependency of tumor cells on angiogenesis, when compared to normal cells, is quantitatively greater than differences in cell replication and cell death, between normal tissue and tumor tissue, which are often exploited in cancer therapy.

Angiogenesis requires copper, as has been shown by numerous studies (Parke et al., *Am. J. Pathol.* 1988, 137: 173–178; Raju et al., *Natl. Cancer Inst.* 1982, 69: 1183–1188; Ziche et al., *Natl. Cancer Inst.* 1982, 69: 475–482; Gullino, *Anticancer Res.* 1986, 6(2): 153–158). Attempts at preventing angiogenesis and hence tumor growth in animal models by reducing in vivo amounts of copper have been reported in the art (Brem et al., *Neurosurgery* 1990, 26:391–396; Brem et al., *Am. J. Pathol.* 1990, 137(5): 1121–1142; Yoshida et al., *Neurosurgery* 1995 37(2): 287–295). These approaches incorporated both copper chelators and low copper diets. More recently, Brewer et al., International Application No. PCT/US99/20374 have shown that the copper chelators, (e.g., tetrathiomolybdate) may be effective in treating diseases (e.g., solid tumor growth), which require angiogenesis.

In addition to the induction of angiogenesis, copper may also have a direct role in tumor cell growth and survival. High copper levels exist in both the plasma and in tumor tissue from patients with many different solid cancers (Chakravarty et al., *J Cancer Res. Clin. Oncol.* 1984, 108: 312–315). Recently, tetrathiomolybdate has been shown to down-regulate the expression of NF-κB as well as inhibit its translocation to the nucleus in the inflammatory breast cancer cell line SUM 149 (Pan et al., *Cancer Res.* 2002, 62: 4854–4859). The NF-κB system may be involved in mediating tumor cell survival and thus its down-regulation in tumor cells by tetrathiomolybdate suggests a direct effect of copper chelation on tumor survival.

Accordingly, novel thiomolybdate compounds, which are copper chelators, are required to fully explore the potential of copper chelators in treating and/or preventing angiogenesis and in tumor cell viability. Such novel thiomolybdate compounds may be effective in treating various diseases associated with angiogenesis such as cancer, copper metabolism disorders neurodegenerative disorders or obesity as well as treating diseases such as inflammatory disorders where the NF-κB pathway is dysregulated.

3. SUMMARY OF THE INVENTION

The present invention satisfies this and other needs by providing novel thiomolybdate derivatives, methods of making novel thiomolybdate derivatives, pharmaceutical compositions of novel thiomolybdate derivatives, methods of using novel thiomolybdate derivatives to treat diseases associated with aberrant vascularization, copper metabolism disorders, neurodegenerative disorders, obesity or NF-κB dysregulation and methods of using pharmaceutical compositions of thiomolybdate derivatives to treat or prevent diseases associated with aberrant vascularization, copper metabolism disorders, neurodegenerative disorders, obesity or NF-κB dysregulation.

In a first aspect, the present invention provides a compound of structural formula (I):

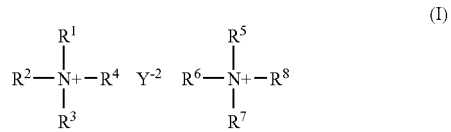

(I)

or a solvate or hydrate or N-oxide thereof wherein:

$R^1$, $R^2$, $R^3$, $R^5$, $R^6$ and $R^7$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, heteroalkyl or substituted heteroalkyl;

R[4] and R[8] are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, heteroalkyl or substituted heteroalkyl or are absent when N is part of an aromatic ring;

optionally, $R^1$ and $R^2$ taken together are alkyldiyl, substituted alkyldiyl, heteroalkyldiyl or substituted heteroalkyldiyl;

optionally, $R^5$ and $R^6$ taken together are alkyldiyl, substituted alkyldiyl, heteroalkyldiyl or substituted heteroalkyldiyl;

optionally, $R^1$ and $R^2$ taken together, $R^2$ and $R^3$ taken together and $R^2$ and $R^4$ taken together are alkyldiyl, substituted alkyldiyl, heteroalkyldiyl or substituted heteroalkyldiyl;

optionally, $R^5$ and $R^6$ taken together, $R^6$ and $R^7$ taken together and $R^6$ and $R^8$ taken together are alkyldiyl, substituted alkyldiyl, heteroalkyldiyl or substituted heteroalkyldiyl;

optionally, $R^3$ and $R^7$ taken together are alkyldiyl, substituted alkyldiyl, heteroalkyldiyl or substituted heteroalkyldiyl; and $Y^{-2}$ is $(MoS_4)^{-2}$, $(Mo_2S_{12})^{-2}$, $(Mo_2S_9)^{-2}$, $(Mo_2S_7)^{-2}$, $(Mo_2S_8)^{-2}$, $(Mo_2S_{11})^{-2}$, $(Mo_2S_6)^{-2}$ or $(Mo_2S_{13})^{-2}$;

with the proviso that if Y is $(MoS_4)^{-2}$ and $R^1$, $R^2$, $R^3$, $R^4$, $R^5$, $R^6$, $R^7$ and $R^8$ are identical then each of $R^1$, $R^2$, $R^3$, $R^4$, $R^5$, $R^6$, $R^7$ and $R^8$ is not hydrogen, methyl, ethyl or n-propyl.

In a second aspect, the present invention provides pharmaceutical compositions of novel thiomolybdate derivatives. The pharmaceutical compositions generally comprise one or more compounds of the invention, pharmaceutically acceptable salts, hydrates or solvates thereof and a pharmaceutically acceptable diluent, carrier, excipient and adjuvant. The choice of diluent, carrier, excipient and adjuvant will depend upon, among other factors, the desired mode of administration.

In a third aspect, the present invention provides methods for treating or preventing diseases characterized by aberrant vascularization, copper metabolism disorders, neurodegenerative disorders, obesity or NF-κB dysregulation. The methods generally involve administering to a patient in need of such treatment or prevention a therapeutically effective amount of a compound and/or pharmaceutical composition of the invention.

In a fourth aspect, the current invention provides pharmaceutical compositions for treating or preventing diseases characterized by aberrant vascularization, copper metabolism disorders, neurodegenerative disorders, obesity or NF-κB dysregulation in a patient in need of such treatment or prevention.

4. BRIEF DESCRIPTION OF THE DRAWINGS

Figure 1:
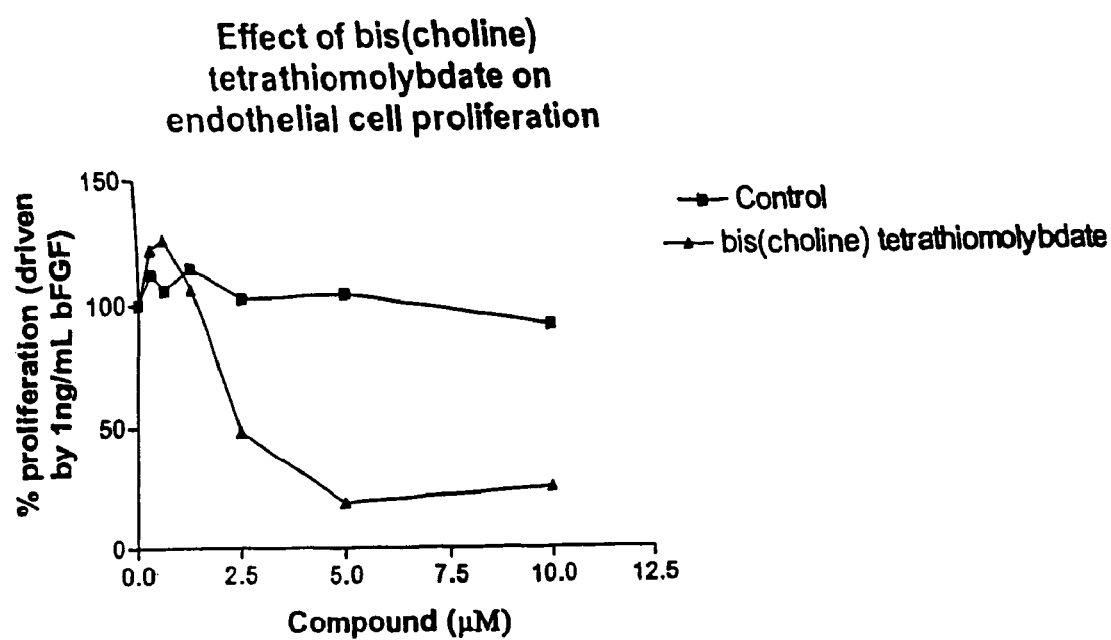
FIG. 1 illustrates the effect of bis(choline) tetrathiomolybdate on endothelial cell production.

5. DETAILED DESCRIPTION OF THE INVENTION 5.1 Definitions

"Compounds of the invention" refers to compounds encompassed by structural formula (I) disclosed herein and includes any specific compounds within that generic formula whose structure is disclosed herein. The compounds of the invention may be identified either by their chemical structure and/or chemical name. When the chemical structure and chemical name conflict, the chemical structure is determinative of the identity of the compound. The compounds of the invention may contain one or more chiral centers and/or double bonds and therefore, may exist as stereoisomers, such as double-bond isomers (i.e., geometric isomers), enantiomers or diastereomers. Accordingly, the chemical structures depicted herein encompass all possible enantiomers and stereoisomers of the illustrated compounds including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds of the invention may also exist in several tautomeric forms including the enol form, the keto form and mixtures thereof. Accordingly, the chemical structures depicted herein encompass all possible tautomeric forms of the illustrated compounds. The compounds of the invention also include isotopically labeled compounds where one or more atoms have an atomic mass different from the atomic mass conventionally found in nature. Examples of isotopes that may be incorporated into the compounds of the invention include, but are not limited to, $^2H$, $^3H$, $^{13}C$, $^{14}C$, $^{15}N$, $^{18}O$ and $^{17}O$. Compounds of the invention may exist in unsolvated forms as well as solvated forms, including hydrated forms and as N-oxides. In general, the hydrated, solvated and N-oxide forms are within the scope of the present invention. Certain compounds of the present invention may exist in multiple crystalline or amorphous forms. In general, all physical forms are equivalent for the uses contemplated by the present invention and are intended to be within the scope of the present invention. Further, it should be understood, when partial structures of the compounds of the invention are illustrated, that brackets indicate the point of attachment of the partial structure to the rest of the molecule.

"Alkyl" by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta- 1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like.

The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. Preferably, an alkyl group comprises from 1 to 20 carbon atoms, more preferably, from 1 to 10 carbon atoms, most preferably, from 1 to 6 carbon atoms.

"Alkanyl" by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl" by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl, cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent, refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" by itself or as part of another substituent, refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. Preferably, the alkyldiyl group is $(C_1-C_{20})$ alkyldiyl, more preferably, $(C_1-C_{10})$ alkyldiyl, most preferably, $(C_1-C_6)$ alkyldiyl. Preferred are saturated acyclic alkanyldiyl groups in which the radical centers are at the terminal carbons, e.g., methandiyl (methano); ethan-1,2-diyl (ethano); propan-1,3-diyl (propano); butan-1,4-diyl (butano); and the like (also referred to as alkyleno, defined infra).

"Alkyleno" by itself or as part of another substituent, refers to a straight-chain alkyldiyl group having two terminal monovalent radical centers derived by the removal of one hydrogen atom from each of the two terminal carbon atoms of straight-chain parent alkane, alkene or alkyne. Typical alkyleno groups include, but are not limited to, methano; ethylenos such as ethano, etheno, ethyno; propylenos such as propano, prop[1]eno, propa[1,2]dieno, prop[1]yno, etc.; butylenos such as butano, but[1]eno, but[2]eno, buta[1,3]dieno, but[1]yno, but[2]yno, but[1,3]diyno, etc.; and the like. Where specific levels of saturation are intended, the nomenclature alkano, alkeno and/or alkyno is used. Preferably, the alkyleno group is $(C_1-C_{20})$ alkyleno, more preferably, $(C_1-C_{10})$ alkyleno, most preferably, $(C_1-C_6)$ alkyleno. Preferred are straight-chain saturated alkano groups, e.g., methano, ethano, propano, butano, and the like.

"Acyl" by itself or as part of another substituent, refers to a radical —C(O)R$^{30}$, where R$^{30}$ is hydrogen, alkyl, cycloalkyl, cycloheteroalkyl, aryl, arylalkyl, heteroalkyl, heteroaryl, heteroarylalkyl as defined herein. Representative examples include, but are not limited to formyl, acetyl, cyclohexylcarbonyl, cyclohexylmethylcarbonyl, benzoyl, benzylcarbonyl and the like.

"Acylamino" by itself or as part of another substituent, refers to a radical —NR$^{31}$C(O)R$^{32}$, where R$^{31}$ and R$^{32}$ are each independently hydrogen, alkyl, cycloalkyl, cycloheteroalkyl, aryl, arylalkyl, heteroalkyl, heteroaryl, heteroarylalkyl, as defined herein. Representative examples include, but are not limited to, formylamino, acetylamino, cylcohexylcarbonylamino, cyclohexylmethyl-carbonylamino, benzoylamino, benzylcarbonylamino and the like.

"Alkoxy" by itself or as part of another substituent, refers to a radical —OR$^{33}$ where R$^{33}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent, refers to a radical —C(O)OR$^{34}$ where R$^{34}$ represents an alkyl or cycloalkyl group as defined herein.

"Aryl" by itself or as part of another substituent, refers to a monovalent aromatic hydrocarbon radical derived by the removal of one hydrogen atom from a single carbon atom of a parent aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. Preferably, an aryl group comprises from 6 to 20 carbon atoms, more preferably from 6 to 12 carbon atoms.

"Arylalkyl" by itself or as part of another substituent, refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. Preferably, an arylalkyl group is ($C_6$–$C_{30}$) arylalkyl, e.g., the alkanyl, alkenyl or alkynyl moiety of the arylalkyl group is ($C_1$–$C_{10}$) and the aryl moiety is ($C_6$–$C_{20}$), more preferably, an arylalkyl group is ($C_6$–$C_{20}$) arylalkyl, e.g., the alkanyl, alkenyl or alkynyl moiety of the arylalkyl group is ($C_1$–$C_8$) and the aryl moiety is ($C_6$–$C_{12}$).

"Cycloalkyl" by itself or as part of another substituent, refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. Preferably, the cycloalkyl group is ($C_3$–$C_{10}$) cycloalkyl, more preferably ($C_3$–$C_7$) cycloalkyl.

"Cycloheteroalkyl" by itself or as part of another substituent, refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkanyl, Heteroalkenyl, Heteroalkanyl, Heteroalkyldiyl and Heteroalkyleno" by themselves or as part of another substituent, refer to alkyl, alkanyl, alkenyl, alkynyl, alkyldiyl and alkyleno groups, respectively, in which one or more of the carbon atoms (and any associated hydrogen atoms) are each independently replaced with the same or different heteroatomic groups. Typical heteroatomic groups which can be included in these groups include, but are not limited to, —O—, —S—, —O—O—, —S—S—, —O—S—, —NR$^{35}$R$^{36}$—, =N—N=, —N=N—, —N=N—NR$^{37}$R$^{38}$, —PR$^{39}$—, —P(O)$_2$—, —POR$^{40}$—, —O—P(O)$_2$—, —SO—, —SO$_2$—, —SnR$^{41}$R$^{42}$— and the like, where R$^{35}$, R$^{36}$, R$^{37}$, R$^{38}$, R$^{39}$, R$^{40}$, R$^{41}$ and R$^{42}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a parent heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. Preferably, the heteroaryl group is from 5–20 membered heteroaryl, more preferably from 5–10 membered heteroaryl. Preferred heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In preferred embodiments, the heteroarylalkyl group is a 6–30 membered heteroarylalkyl, e.g., the alkanyl, alkenyl or alkynyl moiety of the heteroarylalkyl is 1–10 membered and the heteroaryl moiety is a 5–20-membered heteroaryl, more preferably, 6–20 membered heteroarylalkyl, e.g., the alkanyl, alkenyl or alkynyl moiety of the heteroarylalkyl is 1–8 membered and the heteroaryl moiety is a 5–12-membered heteroaryl.

"Parent Aromatic Ring System" by itself or as part of another substituent, refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System" by itself or as part of another substituent, refers to a parent aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "parent heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like.

"Pharmaceutical composition" refers to at least one compound of the invention and a pharmaceutically acceptable vehicle, with which the compound is administered to a patient.

"Pharmaceutically acceptable salt" refers to a salt of a compound of the invention, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Pharmaceutically acceptable vehicle" refers to a diluent, adjuvant, excipient or carrier with which a compound of the invention is administered.

"Patient" includes humans. The terms "human" and "patient" are used interchangeably herein.

"Preventing" or "prevention" refers to a reduction in risk of acquiring a disease or disorder (i.e., causing at least one of the clinical symptoms of the disease not to develop in a patient that may be exposed to or predisposed to the disease but does not yet experience or display symptoms of the disease).

"Prodrug" refers to a derivative of a drug molecule that requires a transformation within the body to release the active drug. Prodrugs are frequently, although not necessarily, pharmacologically inactive until converted to the parent drug. A hydroxyl containing drug may be converted, for example, to a sulfonate, ester or carbonate prodrug, which may be hydrolyzed in vivo to provide the hydroxyl compound. An amino containing drug may be converted, for example, to a carbamate, amide, enamine, imine, N-phosphonyl, N-phosphoryl or N-sulfenyl prodrug, which may be hydrolyzed in vivo to provide the amino compound. A carboxylic acid drug may be converted to an ester (including silyl esters and thioesters), amide or hydrazide prodrug, which be hydrolyzed in vivo to provide the carboxylic acid compound. Prodrugs for drugs which functional groups different than those listed above are well known to the skilled artisan.

"Promoiety" refers to a form of protecting group that when used to mask a functional group within a drug molecule converts the drug into a prodrug. Typically, the promoiety will be attached to the drug via bond(s) that are cleaved by enzymatic or non-enzymatic means in vivo.

"Protecting group" refers to a grouping of atoms that when attached to a reactive functional group in a molecule masks, reduces or prevents reactivity of the functional group. Examples of protecting groups can be found in Green et al., "Protective Groups in Organic Chemistry", (Wiley, 2$^{nd}$ ed. 1991) and Harrison et al., "Compendium of Synthetic Organic Methods", Vols. 1–8 (John Wiley and Sons, 1971–1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Substituted" refers to a group in which one or more hydrogen atoms are independently replaced with the same or different substituent(s). Typical substituents include, but are not limited to, —M, —R$^{60}$, —O$^-$, =O, —OR$^{60}$, —SR$^{60}$, —S$^-$, =S, —NR$^{60}$R$^{61}$, =NR$^{60}$, —CF$_3$, —CN, —OCN, —SCN, —NO, —NO$_2$, =N$_2$, —N$_3$, —S(O)$_2$O$^-$, —S(O)$_2$OH, —S(O)$_2$R$^{60}$, —OS(O$_2$)O$^-$, —OS(O)$_2$R$^{60}$, —P(O)(O$^-$)$_2$, —P(O)(OR$^{60}$)(O$^-$), —OP(O)(OR$^{60}$)(OR$^{61}$), —C(O)R$^{60}$, —C(S)R$^{60}$, —C(O)OR$^{60}$, —C(O)NR$^{60}$R$^{61}$, —C(O)O$^-$, —C(S)OR$^{60}$, —NR$^{62}$C(O)NR$^{60}$R$^{61}$, —NR$^{62}$C(S)NR$^{60}$R$^{61}$, —NR$^{62}$C(NR$^{63}$)NR$^{60}$R$^{61}$ and —C(NR$^{62}$)NR$^{60}$R$^{61}$ where M is independently a halogen; R$^{60}$, R$^{61}$, R$^{62}$ and R$^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally R$^{60}$ and R$^{61}$ together with the nitrogen atom to which they are bonded form a cycloheteroalkyl or substituted cycloheteroalkyl ring; and R$^{64}$ and R$^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally R$^{64}$ and R$^{65}$ together with the nitrogen atom to which they are bonded form a cycloheteroalkyl or substituted cycloheteroalkyl ring.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the patient. In yet another embodiment, "treating" or "treatment" refers to inhibiting the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Therapeutically effective amount" means the amount of a compound that, when administered to a patient for treating a disease, is sufficient to effect such treatment for the disease. The "therapeutically effective amount" will vary depending on the compound, the disease and its severity and the age, weight, etc., of the patient to be treated.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

5.2 Compounds of Structural Formula (I)

In a first embodiment, the compounds of the invention include compound of structural formula (I):

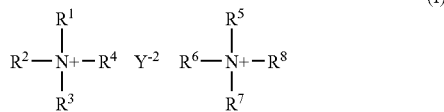

(I)

or a solvate or hydrate or N-oxide thereof wherein:

$R^1$, $R^2$, $R^3$, $R^5$, $R^6$ and $R^7$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, heteroalkyl or substituted heteroalkyl;

$R^4$ and $R^8$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, heteroalkyl or substituted heteroalkyl or are absent when N is part of an aromatic ring;

optionally, $R^1$ and $R^2$ taken together are alkyldiyl, substituted alkyldiyl, heteroalkyldiyl or substituted heteroalkyldiyl;

optionally, $R^5$ and $R^6$ taken together are alkyldiyl, substituted alkyldiyl, heteroalkyldiyl or substituted heteroalkyldiyl;

optionally, $R^1$ and $R^2$ taken together, $R^2$ and $R^3$ taken together and $R^2$ and $R^4$ taken together are alkyldiyl, substituted alkyldiyl, heteroalkyldiyl or substituted heteroalkyldiyl;

optionally, $R^5$ and $R^6$ taken together, $R^6$ and $R^7$ taken together and $R^6$ and $R^8$ taken together are alkyldiyl, substituted alkyldiyl, heteroalkyldiyl or substituted heteroalkyldiyl;

optionally, $R^3$ and $R^7$ taken together are alkyldiyl, substituted alkyldiyl, heteroalkyldiyl or substituted heteroalkyldiyl; and $Y^{-2}$ is $(MoS_4)^{-2}$, $(Mo_2S_{12})^{-2}$, $(Mo_2S_9)^{-2}$, $(Mo_2S_7)^{-2}$, $(Mo_2S_8)^{-2}$, $(Mo_2S_{11})^{-2}$, $(Mo_2S_6)^{-2}$ or $(Mo_2S_{13})^{-2}$;

with the proviso that if Y is $(MoS_4)^{-2}$ and $R^1$, $R^2$, $R^3$, $R^4$, $R^5$, $R^6$, $R^7$ and $R^8$ are identical then each of $R^1$, $R^2$, $R^3$, $R^4$, $R^5$, $R^6$, $R^7$ and $R^8$ is not hydrogen, methyl, ethyl or n-propyl.

Preferably, Y is $(MoS_4)^{-2}$. Preferably, $R^1$, $R^2$, $R^3$, $R^4$, $R^5$, $R^6$, $R^7$ and $R^8$ are not alkyl.

In a third embodiment,

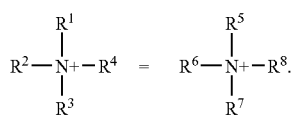

Preferably, Y is $(MoS_4)^{-2}$.

In one embodiment, at least one of $R^1$, $R^2$, $R^3$ and $R^4$ is not alkyl. In another embodiment, $R^1$, $R^2$ and $R^4$ are hydrogen, alkanyl or substituted alkanyl. Preferably, $R^1$, $R^2$ and $R^4$ are hydrogen, methyl or ethyl.

In another embodiment, $R^1$ and $R^2$ are alkanyl. Preferably, $R^1$ and $R^2$ are methyl or ethyl.

In still another embodiment, $R^1$ is alkanyl, substituted alkanyl, alkenyl, substituted alkenyl, aryl, substituted aryl, arylalkyl, substituted arylalkyl, cycloalkyl or substituted cycloalkyl. Preferably, $R^1$ and $R^2$ taken together are alkyleno, substituted alkyleno, heteroalkyleno or substituted heteroalkyleno. More preferably, $R^1$ and $R^2$ taken together are alkyleno or heteroalkyleno.

In still another embodiment, $R^1$ and $R^2$ taken together, $R^2$ and $R^3$ taken together and $R^2$ and $R^4$ taken together are alkyleno, substituted alkyleno, heteroalkyleno or substituted heteroalkyleno. Preferably, $R^1$ and $R^2$ taken together, $R^2$ and $R^3$ taken together and $R^2$ and $R^4$ taken together are alkyleno. Preferably, $R^1(R^2)(R^3)(R^4)N$ has the structure:

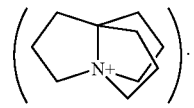

In still another embodiment, $R^3$ and $R^7$ taken together are alkyleno, substituted alkyleno, heteroalkyleno or substituted heteroalkyleno. Preferably, $R^3$ and $R^7$ taken together are alkyleno or heteroalkyleno.

In still another embodiment, $R^1$, $R^2$ and $R^4$ are hydrogen, alkanyl or substituted alkanyl and $R^3$ is alkyl, substituted alkyl, alkenyl, aryl, arylalkyl, cycloalkyl or $R^3$ and $R^7$ taken together are alkyleno, substituted alkyleno, heteroalkyleno or substituted heteroalkyleno. Preferably, $R^1$, $R^2$ and $R^4$ are methyl or ethyl and $R^3$ is alkyl, substituted alkyl, alkenyl, aryl, arylalkyl, cycloalkyl or $R^3$ and $R^7$ taken together are alkyleno or heteroalkyleno. Preferably, $R^1$, $R^2$ and $R^4$ are methyl or ethyl and $R^3$ is alkyl, substituted alkyl, alkenyl, aryl, arylalkyl or cycloalkyl.

In still another embodiment, $R^1(R^2)(R^3)(R^4)N$ is

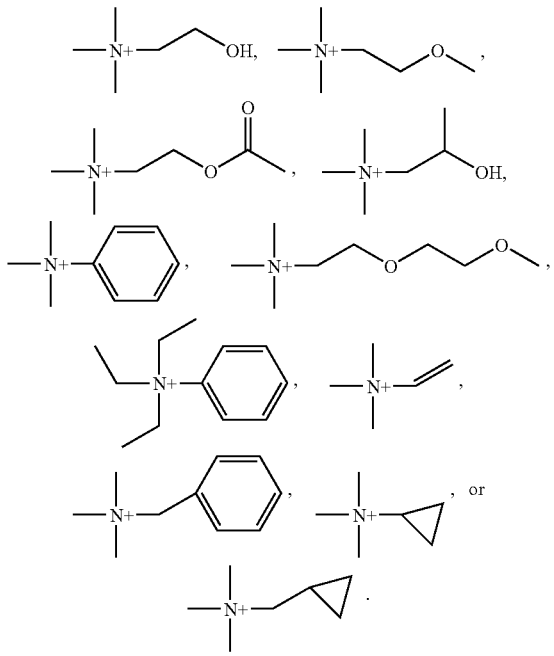

In still another embodiment, $R^1(R^2)(R^3)(R^4)N$ is

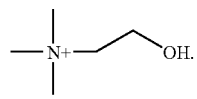

In still another embodiment, $R^1(R^2)(R^3)(R^4)N$ is

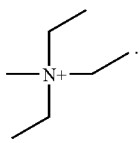

In still another embodiment, $R^1$, $R^2$ and $R^4$ are methyl or ethyl and $R^3$ and $R^7$ taken together are alkyleno or heteroalkyleno. Preferably, $R^1(R^2)(R^3)(R^4)N$ has the structure:

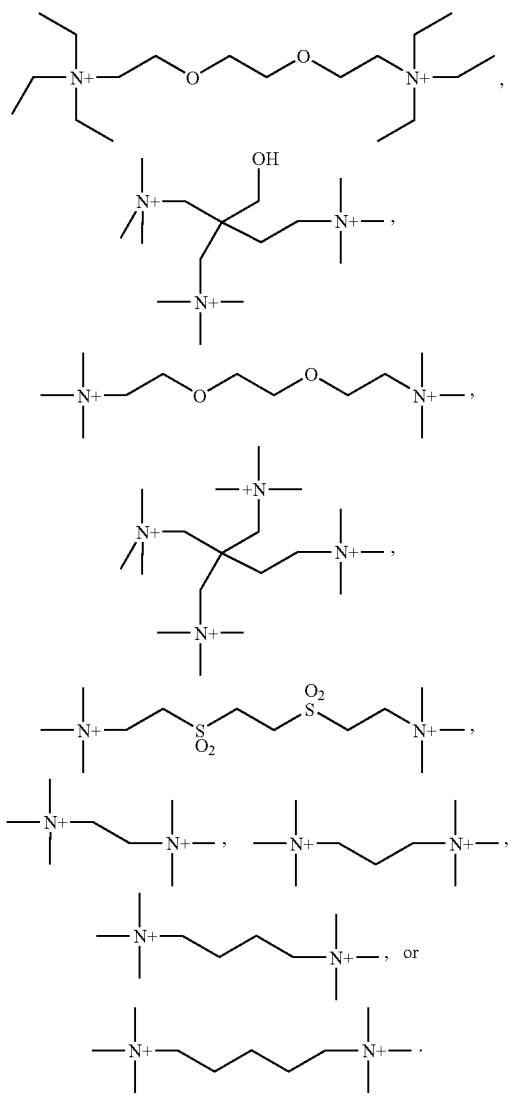

In still another embodiment, $R^1$, $R^2$ and $R^4$ are hydrogen and $R^3$ is substituted alkyl, cycloalkyl or substituted heteroaryl or $R^3$ and $R^7$ taken together are alkyleno. In still another embodiment, $R^1$ and $R^2$ are alkanyl and $R^3$ and $R^4$ are alkyl, substituted alkyl, aryl, arylalkyl or alkyleno. Preferably, $R^1$ and $R^2$ are methyl or ethyl and $R^3$ and $R^4$ are alkyl, substituted alkyl, aryl, arylalkyl or alkyleno.

In still another embodiment, $R^1(R^2)(R^3)(R^4)N$ are

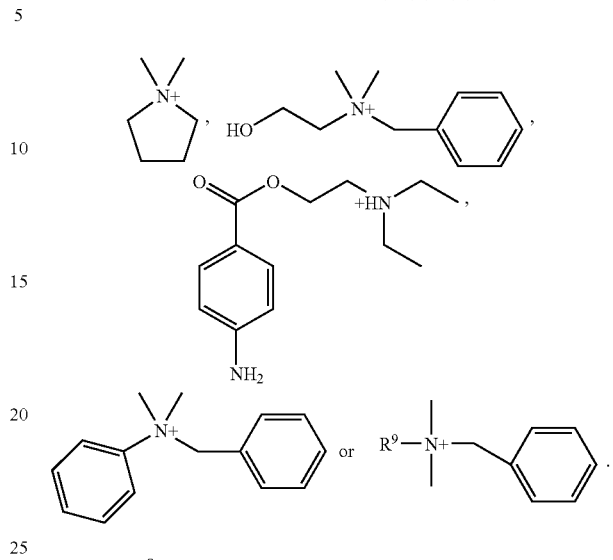

wherein $R^9$ is a mixture of straight chain alkanyl groups which have at least eight carbon atoms and not more than eighteen carbon atoms.

In still another embodiment, $R^1$, $R^2$ and $R^4$ are hydrogen and $R^3$ is substituted alkyl, substituted heteroaryl, cycloalkyl or alkyleno. Preferably, $R^1(R^2)(R^3)(R^4)N$ has the structure:

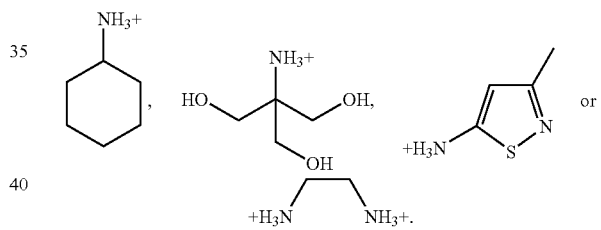

In still another embodiment, $R^1$ and $R^2$ taken together are alkyleno, substituted alkyleno, heteroalkyleno or substituted heteroalkyleno, $R^3$ is alkyl or substituted alkyl and $R^4$ is hydrogen or is absent. Preferably, $R^1(R^2)(R^3)N$ or $R^1(R^2)(R^3)(R^4)N$ has the structure:

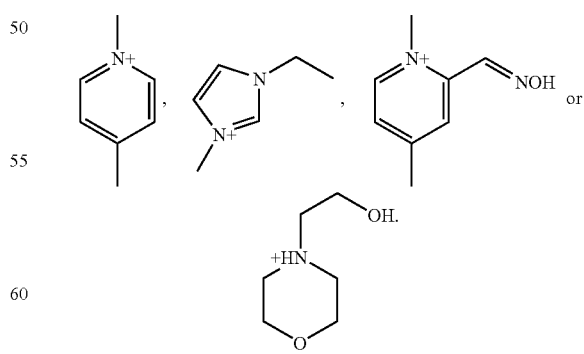

5.3 Synthesis of the Compounds of the Invention

The compounds of the invention may be obtained via conventional synthetic methods illustrated in Schemes 1 and 2. Starting materials useful for preparing compounds of the invention and intermediates thereof are commercially available or can be prepared by well-known synthetic methods. For example, ammonium thiomolybdate may be purchased from well-known chemical suppliers (e.g., Aldrich Chemical Company, Milwaukee, Wis.). Substituted ammonium salts (e.g., ammonium hydroxide and ammonium halides) may be either purchased from commercial sources or may be readily synthesized using well-known synthetic methods (Harrison et al., "Compendium of Synthetic Organic Methods", Vols. 1–8 (John Wiley and Sons, 1971–1996); "Beilstein Handbook of Organic Chemistry," Beilstein Institute of Organic Chemistry, Frankfurt, Germany; Feiser et al., "Reagents for Organic Synthesis," Volumes 1–17, Wiley Interscience; Trost et al., "Comprehensive Organic Synthesis," Pergamon Press, 1991; "Theilheimer's Synthetic Methods of Organic Chemistry," Volumes 1–45, Karger, 1991; March, "Advanced Organic Chemistry," Wiley Interscience, 1991; Larock "Comprehensive Organic Transformations," VCH Publishers, 1989; Paquette, "Encyclopedia of Reagents for Organic Synthesis," John Wiley & Sons, 1995). Other methods for synthesis of the compounds described herein and/or starting materials are either described in the art or will be readily apparent to the skilled artisan. Accordingly, the methods presented in Schemes 1 and 2 herein are illustrative rather than comprehensive.

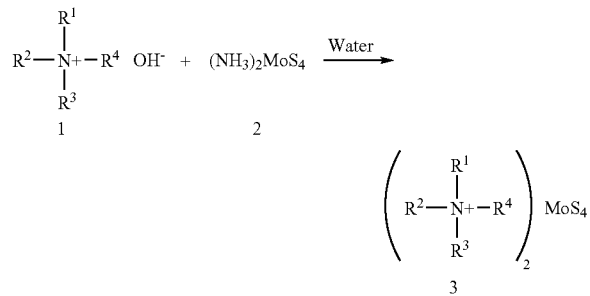

As shown above, in Scheme 1, addition of a quaternary ammonium hydroxide to thiomolybdate in the presence of water leads to cation exchange (equilibrium to product is driven by removal of volatile ammonia) to provide the desired thiomolybdate derivative.

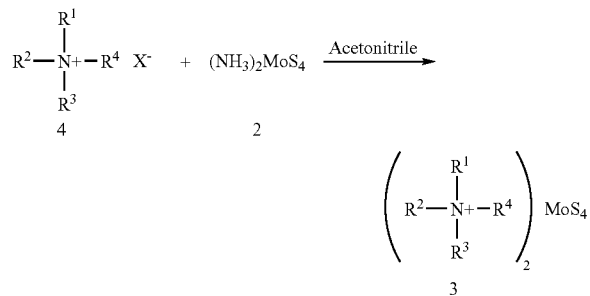

As shown above, in Scheme 2, addition of a quaternary ammonium halide to thiomolybdate in the presence of acetonitrile leads to cation exchange (equilibrium to product is driven by formation of ammonium halide) to provide the desired thiomolybdate derivative.

Thiomolybdate derivatives where the ammonium counterions are different may be prepared from compounds 3 through by treating with one equivalent of another ammonium counterion. Such a reaction would be expected to produce a statistical mixture of products.

5.4 Assays for Compounds of the Invention

Those of skill in the art will appreciate that the in vitro and in vivo assays useful for measuring the activity of the compounds of the invention described herein are illustrative rather than comprehensive.

5.4.1 Assay for Endothelial Cell Migration

For endothelial cell migration, transwells are coated with type I collagen (50 µg/mL) by adding 200 µL of the collagen solution per transwell, then incubating overnight at 37° C. The transwells are assembled in a 24-well plate and a chemoattractant (e.g., FGF-2) is added to the bottom chamber in a total volume of 0.8 mL media. Endothelial cells such as human umbilical vein endothelial cells ("HUVEC"), which have been detached from monolayer culture using trypsin, are diluted to a final concentration of about $10^6$ cells/mL with serum-free media and 0.2 mL of this cell suspension is added to the upper chamber of each transwell. Inhibitors are added to both the upper and lower chambers, and the migration is allowed to proceed for 5 hrs in a humidified atmosphere at 37° C. The transwells are removed from the plate stained using DiffQuik®. Cells which did not migrate are removed from the upper chamber by scraping with a cotton swab and the membranes are detached, mounted on slides, and counted under a high-power field (400×) to determine the number of cells migrated.

5.4.2 Biological Assay of Anti-Invasive Activity

The compounds and/or compositions of the invention are tested for their anti-invasive capacity. The ability of cells such as endothelial cells or tumor cells (e.g., PC-3 human prostatic carcinoma) cells to invade through a reconstituted basement membrane (Matrigel®) in an assay known as a Matrigel® invasion assay (Kleinman et al., *Biochemistry* 1986, 25: 312–318; Parish et al., *Int. J. Cancer* 1992, 52:378–383). Matrigel® is a reconstituted basement membrane containing type IV collagen, laminin, heparan sulfate proteoglycans such as perlecan, which bind to and localize bFGF, vitronectin as well as transforming growth factor-β (TGFβ, urokinase-type plasminogen activator (uPA), tissue plasminogen activator (tPA), and the serpin known as plasminogen activator inhibitor type 1 (PAI-1) (Chambers et al., *Canc. Res.* 1995, 55:1578–1585). Results obtained in this assay for compounds which target extracellular receptors or enzymes are typically predictive of the efficacy of these compounds in vivo (Rabbani et al., 1995, Int. J. Cancer 63: 840–845).

Such assays employ transwell tissue culture inserts. Invasive cells are defined as cells which are able to traverse through the Matrigel® and upper aspect of a polycarbonate membrane and adhere to the bottom of the membrane. Transwells (Costar) containing polycarbonate membranes (8.0 µm pore size) are coated with Matrigel® (Collaborative Research), which has been diluted in sterile PBS to a final concentration of 75 µg/mL (60 µL of diluted Matrigel® per insert), and placed in the wells of a 24-well plate. The membranes are dried overnight in a biological safety cabinet, then rehydrated by adding 100 µL of DMEM containing antibiotics for 1 hour on a shaker table. The DMEM is removed from each insert by aspiration and 0.8 mL of DMEM/10% FBS/antibiotics is added to each well of the 24-well plate such that it surrounds the outside of the transwell ("lower chamber"). Fresh DMEM/antibiotics (100 µL), human Glu-plasminogen (5 µg/mL), and any inhibitors to be tested are added to the top, inside of the transwell ("upper chamber"). The cells which are to be tested are trypsinized and resuspended in DMEM/antibiotics, then added to the top chamber of the transwell at a final concentration of 800,000 cells/mL. The final volume of the upper chamber is adjusted to 200 µL. The assembled plate is then incubated in a humid 5% $CO_2$ atmosphere for 72 hours. After incubation, the cells are fixed and stained using DiffQuik® (Giemsa stain) and the upper chamber is then scraped using a cotton swab to remove the Matrigel® and any cells which did not invade through the membrane. The membranes are detached from the transwell using an X-acto® blade, mounted on slides using Permount® and cover-slips, then counted under a high-powered (400×) field. An average of the cells invaded is determined from 5–10 fields counted and plotted as a function of inhibitor concentration.

5.4.3 Tube-Formation Assays of Anti-Angiogenic Activity

The compounds of the invention may be tested for anti-angiogenic activity in one of two different assay systems in vitro.

Endothelial cells, for example, human umbilical vein endothelial cells ("HUVEC") or human microvascular endothelial cells ("HMVEC") which can be prepared or obtained commercially, are mixed at a concentration of $2 \times 10^5$ cells/mL with fibrinogen (5 mg/mL in phosphate buffered saline ("PBS") in a 1:1 (v/v) ratio. Thrombin is added (5 units/mL final concentration) and the mixture is immediately transferred to a 24-well plate (0.5 mL per well). The fibrin gel is allowed to form and then VEGF and bFGF are added to the wells (each at 5 ng/mL final concentration) along with the test compound. The cells are incubated at 37° C. in 5% $CO_2$ for 4 days at which time the cells in each well are counted and classified as either rounded, elongated with no branches, elongated with one branch, or elongated with 2 or more branches. Results are expressed as the average of 5 different wells for each concentration of compound. Typically, in the presence of angiogenic inhibitors, cells remain either rounded or form undifferentiated tubes (e.g., 0 or 1 branch). This assay is recognized in the art to be predictive of angiogenic (or anti-angiogenic) efficacy in vivo (Min et al., *Cancer Res.* 1996 56: 2428–2433).

In an alternate assay, endothelial cell tube formation is observed when endothelial cells are cultured on Matrigel(& (Schnaper et al., *J. Cell. Physiol.* 1995 165:107–118). Endothelial cells ($1 \times 10^4$ cells/well) are transferred onto Matrigel®-coated 24-well plates and tube formation is quantitated after 48 hours. Inhibitors are tested by addition at either the same time as the endothelial cells or at various time points thereafter. Tube formation can also be stimulated by adding angiogenic growth factors such as bFGF or VEGF, differentiation stimulating agents (e.g., PMA) or combinations thereof.

This assay models angiogenesis by presenting a particular type of basement membrane to the endothelial cells, namely the layer of matrix which migrating and differentiating endothelial cells might be expected to first encounter. In addition to bound growth factors, the matrix components found in Matrigel® (and in basement membranes in situ) or proteolytic products thereof may also be stimulatory for endothelial cell tube formation which makes this model complementary to the fibrin gel angiogenesis model previously described (Blood et al., *Biochim. Biophys. Acta* 1990, 1032:89–118; Odedra et al., *Pharmac. Ther.* 1991, 49:111–124). The compounds of this invention inhibit endothelial cell tube formation in both assays, which suggests that the compounds will also have anti-angiogenic activity.

5.4.4 Assays for Inhibition of Proliferation

The ability of the compounds of the invention to inhibit the proliferation of endothelial cells may be determined in a 96-well format. Type I collagen (gelatin) is used to coat the wells of the plate (0.1–1 mg/mL in PBS, 0.1 mL per well for 30 minutes at room temperature). After washing the plate (3× w/PBS), 3–6,000 cells are plated per well and allowed to attach for 4 hours (37° C./5% $CO_2$) in Endothelial Growth Medium (EGM; Clonetics) or M199 media containing 0.1–2% FBS. The media and any unattached cells are removed at the end of 4 hours and fresh media containing bFGF (1–10 ng/mL) or VEGF (1–10 ng/mL) is added to each well. Compounds to be tested are added last and the plate is allowed to incubate (37° C./5% $CO_2$) for 24–48 hrs. MTS (Promega) is added to each well and allowed to incubate from 1–4 hrs. The absorbance at 490 nm, which is proportional to the cell number, is then measured to determine the differences in proliferation between control wells and those containing test compounds. A similar assay system can be set up with cultured adherent tumor cells. However, collagen may be omitted in this format. Tumor cells (e.g., 3,000–10,000/well) are plated and allowed to attach overnight. Serum free medium is then added to the wells, and the cells are synchronized for 24 hrs. Medium containing 10% FBS is then added to each well to stimulate proliferation. Compounds to be tested are included in some of the wells. After 24 hrs, MTS is added to the plate and the assay developed and read as described above. A similar methodology may also be employed to evaluate the effects of the compounds of the invention on the proliferation of other cell types including tumor cells except that VEGF and bFGF would not be used to stimulate growth of the cells. If there is evidence of anti-proliferative activity, induction of apoptosis may be measured using TumorTACS (Genzyme).

5.4.5 Assays of Cytotoxicity

The cytotoxic effects of the compounds of the invention may be determined for various cell types including tumor cells, endothelial cells, fibroblasts and macrophages.

A typical assay would involve plating cells at a density of 5–10,000 cells per well in a 96-well plate. The compound to be tested is added at a variety of concentrations and allowed to incubate with the cells for 24 hours. The cells are washed 3× with media. For cytotoxicity assays (measuring cell lysis), a Promega 96-well cytotoxicity kit is used.

5.4.6 Corneal Angiogenesis Model

The protocol used is essentially identical to that described by Volpert et al., *J. Clin. Invest.* 1996, 98:671–679. Briefly, female Fischer rats (120–140 gms) are anesthetized and pellets (5 µl) comprised of Hydron®, bFGF (150 nM), and the compounds to be tested are implanted into tiny incisions made in the cornea 1.0–1.5 mm from the limbus. Neovascularization is assessed at 5 and 7 days after implantation. On day 7, animals are anesthetized and infused with a dye such as colloidal carbon to stain the vessels. The animals are then euthanized, the corneas fixed with formalin, and the corneas flattened and photographed to assess the degree of neovascularization. Neovessels may be quantitated by imaging the total vessel area or length or simply by counting vessels.

5.4.7 Matrigel® Plug Assay

This assay is performed essentially as described by Passaniti et al., *Lab Invest.* 1992, 67:519–528. Ice-cold Matrigel® (e.g., 500 µL) (Collaborative Biomedical Products, Inc., Bedford, Mass.) is mixed with heparin (e.g., 50 µg/ml), FGF-2 (e.g., 400 ng/ml) and the compound to be tested. In some assays, bFGF may be substituted with tumor cells as the angiogenic stimulus. The Matrigel® mixture is injected subcutaneously into 4–8 week-old athymic nude mice at sites near the abdominal midline, preferably 3 injections per mouse. The injected Matrigel® forms a palpable solid gel. Injection sites are chosen such that each animal receives a positive control plug (such as FGF-2+ heparin), a negative control plug (e.g., buffer+ heparin) and a plug that includes the compound being tested for its effect on angiogenesis (e.g., FGF-2+ heparin+ compound). All treatments are preferably run in triplicate. Animals are sacrificed by cervical dislocation at about 7 days post injection or another time that may be optimal for observing angiogenesis. The mouse skin is detached along the abdominal midline, and the Matrigel® plugs are recovered and scanned immediately at high resolution. Plugs are then dispersed in water and incubated at 37° C. overnight. Hemoglobin (Hb) levels are determined using Drabkin's solution (e.g., obtained from Sigma) according to the manufacturers' instructions. The amount of Hb in the plug is an indirect measure of angiogenesis as it reflects the amount of blood in the sample. In addition, or alternatively, animals may be injected prior to sacrifice with a 0.1 ml buffer (preferably PBS) containing a high molecular weight dextran to which is conjugated a fluorophore. The amount of fluorescence in the dispersed plug, determined fluorimetrically and also serves as a measure of angiogenesis in the plug. Staining with mAb anti-CD31 (CD31 is platelet-endothelial cell adhesion molecule or "PECAM") may also be used to confirm neovessel formation and microvessel density in the plugs.

5.4.8 Chick Chorioallantoic Membrane (CAM) Angiogenesis Assay

This assay is performed essentially as described by Nguyen et al., *Microvascular Res.* 1994, 47:31–40. A mesh containing either angiogenic factors (bFGF) or tumor cells plus inhibitors is placed onto the CAM of an 8-day old chick embryo and the CAM observed for 3–9 days after implantation of the sample. Angiogenesis is quantitated by determining the percentage of squares in the mesh which contain blood vessels.

5.4.9 In Vivo Assessment Angiogenesis Inhibition and Anti-Tumor Effects Using the Matrigel® Plug Assay with Tumor Cells In this assay, tumor cells, for example, $1-5\times10^6$ cells of the 3LL Lewis lung carcinoma or the rat prostate cell line MatLyLu, are mixed with Matrigel® and then injected into the flank of a mouse following the protocol described in section 5.4.7 above. A mass of tumor cells and a powerful angiogenic response can be observed in the plugs after about 5 to 7 days. The anti-tumor and anti-angiogenic action of a compound in an actual tumor environment can be evaluated by including it in the plug. Measurement is then made of tumor weight, Hb levels or fluorescence levels (of a dextran-fluorophore conjugate injected prior to sacrifice). To measure Hb or fluorescence, the plugs are first homogenize with a tissue homogenizer.

5.4.10 Xenograft Model of Subcutaneous Tumor Growth

Nude mice are inoculated with MDA-MB-231 cells (human breast carcinoma) and Matrigel® ($1\times10^6$ cells in 0.2 mL) subcutaneously in the right flank of the animals. The tumors are staged to 200 $mm^3$ and then treatment with a test compound is initiated. Tumor volumes are obtained every other day and the animals are sacrificed after 2 weeks of treatment. The tumors are excised, weighed and paraffin embedded. Histological sections of the tumors are analyzed by H and E, anti-CD31, Ki-67, TUNEL, and CD68 staining.

Other human tumor cell lines including but not limited to PC-3, CWR22R, SK-OV-3, A2780, A549, HCT116, HT29 may also be use3d to test the anti-tumor activity of the compounds of the invention in a similar manner.

5.4.11 Xenograft Model of Metastasis

The compounds of the invention may also be tested for inhibition of late metastasis using an experimental metastasis model (Crowley et al., *Proc. Natl. Acad. Sci. USA* 1993, 90 5021–5025). Late metastasis involves the steps of attachment and extravasation of tumor cells, local invasion, seeding, proliferation and angiogenesis. Human prostatic carcinoma cells (PC-3) transfected with a reporter gene, preferably the green fluorescent protein (GFP) gene, but as an alternative with a gene encoding the enzymes chloramphenicol acetyl-transferase (CAT), luciferase or LacZ, are inoculated into nude mice. This approach permits utilization of either of these markers (fluorescence detection of GFP or histochemical colorimetric detection of enzymatic activity) to follow the fate of these cells. Cells are injected, preferably i.v., and metastases identified after about 14 days, particularly in the lungs but also in regional lymph nodes, femurs and brain. This mimics the organ tropism of naturally occurring metastases in human prostate cancer. For example, GFP-expressing PC-3 cells ($1\times10^6$ cells per mouse) are injected i.v. into the tail veins of nude (nu/nu) mice. Animals are treated with a test composition at 100 µg/animal/day given q.d. IP. Single metastatic cells and foci are visualized and quantitated by fluorescence microscopy or light microscopic histochemistry or by grinding the tissue and quantitative calorimetric assay of the detectable label.

5.4.12 Inhibition of Spontaneous Metastasis In Vivo by HPRG and Functional Derivatives The rat syngeneic breast cancer system (Xing et al., *Int. J. Cancer* 67:423–429 (1996) employs Mat BIII rat breast cancer cells. Tumor cells, for example about $10^6$ suspended in 0.1 mL PBS, are inoculated into the mammary fat pads of female Fisher rats. At the time of inoculation, a 14-day Alza osmotic mini-pump is implanted intraperitoneally to dispense the test compound. The compound is dissolved in PBS (e.g., 200 mM stock), sterile filtered and placed in the minipump to achieve a release rate of about 4 mg/kg/day. Control animals receive vehicle (PBS) alone or a vehicle control peptide in the mini-pump. Animals are sacrificed at about day 14.

Other models of experimental metastasis may also be used to evaluate the compounds of the invention. These models would utilize the human tumor cell lines described supra injected IV through the tail vein of a nude mouse. Typically, these mice are sacrificed 28 days after tumor cell inoculation and their lungs evaluated for the presence of metastases.

5.4.13 3LL Lewis Lung Carcinoma: Primary Tumor Growth

This tumor line arose spontaneously in 1951 as carcinoma of the lung in a C57BL/6 mouse (*Cancer Res.* 1955, 15:39. See, also Malave et al., *J. Nat'l. Canc. Inst.* 1979, 62:83–88). It is propagated by passage in C57BL/6 mice by subcutaneous inoculation and is tested in semiallogeneic C57BL/6×DBA/2 $F_1$ mice or in allogeneic C3H mice. Typically six animals per group for subcutaneously implant, or ten for intramuscular implant are used. Tumor may be implanted by subcutaneous inoculation as a 2–4 mm fragment, or intramuscularly implanted or subcutaneous implanted as an inoculum of suspended cells of about $0.5$–$2 \times 10^6$-cells. Treatment begins 24 hours after implant or is delayed until a tumor of specified size (usually approximately 400 mg) can be palpated. The test compound is administered ip daily for 11 days Animals are followed by weighing, palpation, and measurement of tumor size. Typical tumor weight in untreated control recipients on day 12 after intramuscular inoculation is 500–2500 mg. Typical median survival time is 18–28 days. A positive control compound, for example cyclophosphamide at 20 mg/kg/injection per day on days 1–11 is used. Results computed include mean animal weight, tumor size, tumor weight, survival time. For confirmed therapeutic activity, the test composition should be tested in two multidose assays.

5.4.13 3LL Lewis Lung Carcinoma: Primary Growth and Spontaneous Metastasis Model This model has been utilized by a number of investigators (See, for example, Gorelik et al., 1980, *J. Nat'l. Canc. Inst.* 65:1257–1264; Gorelik et al., 1980, *Rec. Results Canc. Res.* 75:20–28; Isakov et al., *Invasion Metas.* 1982, 2:12–32; Talmadge et al., *J. Nat'l. Canc. Inst.* 1982, 69:975–980; Hilgard et al., *Br. J. Cancer* 1977, 35:78–86). Test mice are male C57BL/6 mice, 2–3 months old. Following subcutaneous, intramuscular or intra-footpad implantation, this tumor produces metastases, preferentially in the lungs. With some lines of the tumor, the primary tumor exerts antimetastatic effects and must first be excised before study of the metastatic phase (see also, U.S. Pat. No. 5,639,725).

Single-cell suspensions are prepared from solid tumors by treating minced tumor tissue with a solution of 0.3% trypsin. Cells are washed 3 times with PBS (pH 7.4) and suspended in PBS. Viability of the 3LL cells prepared in this way is generally about 95–99% (by trypan blue dye exclusion). Viable tumor cells ($3 \times 10^4$–$5 \times 10^6$) suspended in 0.05 ml PBS are injected subcutaneously, either in the dorsal region or into one hind foot pad of C57BL/6 mice. Visible tumors appear after 3–4 days after dorsal sc injection of $10^6$ cells. The day of tumor appearance and the diameters of established tumors are measured by caliper every two days.

The treatment is given as one or two doses of peptide or derivative, per week. In another embodiment, the peptide is delivered by osmotic minipump.

In experiments involving tumor excision of dorsal tumors, when tumors reach about 1500 mm$^3$ in size, mice are randomized into two groups: (1) primary tumor is completely excised; or (2) sham surgery is performed and the tumor is left intact. Although tumors from 500–3000 mm$^3$ inhibit growth of metastases, 1500 mm$^3$ is the largest size primary tumor that can be safely resected with high survival and without local regrowth. After 21 days, all mice are sacrificed and autopsied.

Lungs are removed and weighed. Lungs are fixed in Bouin's solution and the number of visible metastases is recorded. The diameters of the metastases are also measured using a binocular stereoscope equipped with a micrometer-containing ocular under 8× magnification. On the basis of the recorded diameters, it is possible to calculate the volume of each metastasis. To determine the total volume of metastases per lung, the mean number of visible metastases is multiplied by the mean volume of metastases. To further determine metastatic growth, it is possible to measure incorporation of $^{125}$IdUrd into lung cells (Thakur et al., *J. Lab. Clin. Med.* 1977, 89:217–228). Ten days following tumor amputation, 25 μg of fluorodeoxyuridine is inoculated into the peritoneums of tumor-bearing (and, if used, tumor-resected mice). After 30 min, mice are given 1 μCi of $^{125}$IdUrd (iododeoxyuridine). One day later, lungs and spleens are removed and weighed, and a degree of $^{125}$IdUrd incorporation is measured using a gamma counter.

In mice with footpad tumors, when tumors reach about 8–10 mm in diameter, mice are randomized into two groups: (1) legs with tumors are amputated after ligation above the knee joints; or (2) mice are left intact as nonamputated tumor-bearing controls. (Amputation of a tumor-free leg in a tumor-bearing mouse has no known effect on subsequent metastasis, ruling out possible effects of anesthesia, stress or surgery). Mice are killed 10–14 days after amputation. Metastases are evaluated as described above.

5.5 Therapeutic Uses

In accordance with the invention, a compound of structural formula (I) and/or a pharmaceutical composition thereof is administered to a patient, preferably a human, suffering from a disease characterized by aberrant vascularization. Aberrant vascularization includes abnormal neovascularization such as the formation of new blood vessels, larger blood vessels, more branched blood vessels and any other mechanism, which leads to an increased blood carrying capacity to a diseased tissue or site. The compounds and pharmaceutical compositions of the invention treat aberrant vascularization.

Preferably, diseases characterized by aberrant vascularization include cancer (e.g., any vascularized tumor, preferably, a solid tumor, including but not limited to, carcinomas of the lung, breast, ovary, stomach, pancreas, larynx, esophagus, testes, liver, parotid, bilary tract, colon, rectum, cervix, uterus, endometrium, kidney, bladder, prostrate, thyroid, squamous cell carcinomas, adenocarcinomas, small cell carcinomas, melanomas, gliomas, neuroblastomas, sarcomas (e.g., angiosarcomas, chondrosarcomas)), arthritis, diabetes, arteriosclerosis, arteriovenous, malformations, corneal graft neovascularization, delayed wound healing, diabetic retinopathy, age related macular degeneration, granulations, burns, hemophilic joints, rheumatoid arthritis, hypertrophic scars, neovascular glaucoma, nonunion fractures, Osier Weber Syndrome, psoriasis, granuloma, retrolental fibroplasia, pterygium, scleroderma, trachoma, vascular adhesions, ocular neovascularization, parasitic diseases, hypertrophy following surgery, inhibition of hair growth, macular degeneration (including both wet and dry type), rheumatoid arthritis and osteoarthritis. More preferably, diseases characterized by aberrant vascularization include cancer, macular degeneration and rheumatoid arthritis.

Further, in accordance with the invention, a compound of structural formula (I) and/or a pharmaceutical composition thereof may be administered to a patient, preferably a human, suffering from a disease associated with copper metabolism disorders (e.g., Wilson's disease) to treat such a disease.

Still further, in accordance with the invention, a compound of structural formula (I) and/or a pharmaceutical composition thereof may be administered to a patient, preferably a human, to treat obesity. The compounds of structural formula (I) may be also used to reduce levels of inflammatory cytokines (e.g., TNF-α, TNF-β, IL-8, etc.) and plasminogen activator inhibitor, which may be associated with angiogenesis and obesity (Loskutoff et al., *Ann. N.Y. Acad. Sci.*, 2000, 902:272–281; Pan et al., *Cancer Res.*, 2002, 62:4854–4859; Hanada et al., *Cytokine Growth Factor Rev.* 2002, 13: 413–421; Chen et al., *Science* 2002, 296: 1634–5; Miyake et al., *J. Neuropathol. Exp. Neurol.* 59:18–28; Koch et al., *Science* 1992, 258:1798–801; Osawa et al., *Infect. Immun.* 2002, 70:6294–6301; Bajou et al., *Nat. Med.* 1998, 4 923–8).

Still further, in accordance with the invention, a compound of structural formula (I) and/or a pharmaceutical composition thereof may be administered to a patient, preferably a human, suffering from a neurodegenerative disorder, to treat the neurodegenerative disorder. Elevated levels of copper have been reported in the art to mediate the pathobiology of various neurodegenerative disorders including Alzheimer's disease, amyotrophic lateral sclerosis (ALS) and prion disease (Llanos et al., *DNA Cell Biol.* 2002, 21: 259–270; Carri et al., *Funct. Neurol* 2001, 16:181–188; Perry et al., *CNS Drugs* 2002, 16:339–352; Kowalik-Jankowska et al., *Environ Health Perspect,* 2002, 5: 869–870; Maynard et al., *J. Biol. Chem.* Sep. 4, 2002; Gnjec et al., *Front Biosci.* 2002, 16–23; Strausak et al., *Brain Res. Bull.* 2001 55: 175–185; Brown, *Brain Res. Bull.* 2001, 55:165–173; Brown, *Biochem. Soc. Trans* 2002, 30:742–745).

Still further, in accordance with the invention, a compound of structural formula (I) and/or a pharmaceutical composition thereof may be administered to a patient, preferably a human, to treat diseases characterized by dysregulated activity of the NF-κB or dysregulated inflammation of inflammatory response.

Further, in certain embodiments, a compounds of the invention and and/or pharmaceutical compositions thereof are administered to a patient, preferably a human, as a preventative measure against various diseases or disorders characterized by aberrant vascularization, copper metabolism disorders, neurodegenerative disorders, obesity or NF-κB dysregulation. Accordingly, compounds of structural Formula (I) and/or pharmaceutical compositions thereof may be used for the prevention of one disease or disorder and concurrently treating another (e.g., preventing Wilson's disease or Alzheimer's while treating cancer).

The suitability of the compounds of structural Formula (I) and/or pharmaceutical compositions of compounds of Formula (I) in treating or preventing various diseases or disorders characterized by aberrant vascularization, copper metabolism disorders, neurodegenerative disorders, obesity or NF-κB dysregulation may be determined by methods described in the art and herein. Accordingly, it is well with the capability of those of skill in the art to assay and use the compounds of structural Formula (I) and/or pharmaceutical compositions thereof to treat or prevent aberrant vascularization, copper metabolism disorders, neurodegenerative disorders, obesity or NF-κB dysregulation.

5.6 Therapeutic/Prophylactic Administration

The compounds and/or pharmaceutical compositions of the invention may be advantageously used in human medicine. As previously described in Section 5.4 above, compounds of structural Formula (I) and/or pharmaceutical compositions thereof are useful for the treatment or prevention of various diseases characterized by aberrant vascularization, copper metabolism disorders, neurodegenerative disorders and obesity.

When used to treat or prevent the above diseases or disorders, compounds and/or pharmaceutical compositions of the invention may be administered or applied singly, or in combination with other agents. The compounds and/or pharmaceutical compositions of the invention may also be administered or applied singly, in combination with other pharmaceutically active agents (e.g., other anti-cancer agents, other anti-angiogenic agents, other chelators such as zinc, penicillamine, etc. and other anti-obesity agents), including other compounds of the invention.

The current invention provides methods of treatment and prophylaxis by administration to a patient of a therapeutically effective amount of a pharmaceutical composition and/or compound of the invention. The patient may be an animal, more preferably, is a mammal and most preferably is a human.

The present compounds and/or pharmaceutical compositions of the invention, which comprise one or more compounds of the invention, are preferably administered orally. The compounds and/or pharmaceutical compositions of the invention may also be administered by any other convenient route, for example, by infusion or bolus injection, by absorption through epithelial or mucocutaneous linings (e.g., oral mucosa, rectal and intestinal mucosa, etc.). Administration can be systemic or local. Various delivery systems are known, (e.g., encapsulation in liposomes, microparticles, microcapsules, capsules, etc.) that can be used to administer a compound and/or pharmaceutical composition of the invention. Methods of administration include, but are not limited to, intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The preferred mode of administration is left to the discretion of the practitioner and will depend in-part upon the site of the medical condition. In most instances, administration will result in the release of the compounds and/or pharmaceutical compositions of the invention into the bloodstream.

In specific embodiments, it may be desirable to administer one or more compounds and/or pharmaceutical composition of the invention locally to the area in need of treatment. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In one embodiment, administration can be by direct injection at the site (or former site) of cancer or arthritis.

In certain embodiments, it may be desirable to introduce one or more compounds and/or pharmaceutical compositions of the invention into the central nervous system by any suitable route, including intraventricular, intrathecal and epidural injection. Intraventricular injection may be facilitated by an intraventricular catheter, for example, attached to a reservoir, such as an Ommaya reservoir.

A compound and/or pharmaceutical composition of the invention may also be administered directly to the lung by inhalation. For administration by inhalation, a compound and/or pharmaceutical composition of the invention may be conveniently delivered to the lung by a number of different devices. For example, a Metered Dose Inhaler ("MDI"), which utilizes canisters that contain a suitable low boiling propellant, (e.g., dichlorodifluoromethane, trichlorofluoromethane, dichlorotetrafluoroethane, carbon dioxide or any other suitable gas) may be used to deliver compounds of the invention directly to the lung.

Alternatively, a Dry Powder Inhaler ("DPI") device may be used to administer a compound and/or pharmaceutical composition of the invention to the lung. DPI devices typically use a mechanism such as a burst of gas to create a cloud of dry powder inside a container, which may then be inhaled by the patient. DPI devices are also well known in the art. A popular variation is the multiple dose DPI ("MD-DPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator may be formulated containing a powder mix of a compound of the invention and a suitable powder base such as lactose or starch for these systems.

Another type of device that may be used to deliver a compound and/or pharmaceutical composition of the invention to the lung is a liquid spray device supplied, for example, by Aradigm Corporation. Liquid spray systems use extremely small nozzle holes to aerosolize liquid drug formulations that may then be directly inhaled into the lung.

In one embodiment, a nebulizer is used to deliver a compound and/or pharmaceutical composition of the invention to the lung. Nebulizers create aerosols from liquid drug formulations by using, for example, ultrasonic energy to form fine particles that may be readily inhaled (see e.g., Verschoyle et al., *British J. Cancer*, 1999, 80, Suppl. 2, 96, which is herein incorporated by reference). Examples of nebulizers include devices supplied by Sheffield/Systemic Pulmonary Delivery Ltd. (See, Armer et al., U.S. Pat. No. 5,954,047; van der Linden et al., U.S. Pat. No. 5,950,619; van der Linden et al., U.S. Pat. No. 5,970,974), Aventis and Batelle Pulmonary Therapeutics.

In another embodiment, an electrohydrodynamic ("EHD") aerosol device is used to deliver a compound and/or pharmaceutical composition of the invention to the lung. EHD aerosol devices use electrical energy to aerosolize liquid drug solutions or suspensions (see e.g., Noakes et al., U.S. Pat. No. 4,765,539). The electrochemical properties of the formulation may be important parameters to optimize when delivering a compound and/or pharmaceutical composition of the invention to the lung with an EHD aerosol device and such optimization is routinely performed by one of skill in the art. EHD aerosol devices may more efficiently deliver drugs to the lung than existing pulmonary delivery technologies.

In another embodiment, the compounds and/or pharmaceutical compositions of the invention can be delivered in a vesicle, in particular a liposome (See, Langer, 1990, *Science*, 249:1527–1533; Treat et al., in "Liposomes in the Therapy of Infectious Disease and Cancer," Lopez-Berestein and Fidler (eds.), Liss, N.Y., pp. 353–365 (1989); see generally "Liposomes in the Therapy of Infectious Disease and Cancer," Lopez-Berestein and Fidler (eds.), Liss, New York, pp. 353–365 (1989)).

In another embodiment, the compounds and/or pharmaceutical compositions of the invention can be delivered via sustained release systems, preferably oral sustained release systems. In one embodiment, a pump may be used (See, Langer, supra; Sefton, 1987, *CRC Crit Ref Biomed Eng.* 14:201; Saudek et al., 1989, *N. Engl. J. Med.* 321:574).

In another embodiment, polymeric materials can be used (see "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Langer et al., 1983, *J Macroinol. Sci. Rev. Macromol Chem.* 23:61; see also Levy et al., 1985, *Science* 228: 190; During et al., 1989, *Ann. Neurol.* 25:351; Howard et al., 1989, *J. Neurosurg.* 71:105). In another embodiment, polymeric materials are used for oral sustained release delivery. Preferred polymers include sodium carboxymethylcellulose, hydroxypropylcellulose, hydroxypropylmethylcellulose and hydroxyethylcellulose (most preferred, hydroxypropyl methylcellulose). Other preferred cellulose ethers have been described (Alderman, *Int. J. Pharm. Tech. & Prod. Mfr.*, 1984, 5(3) 1–9). Factors affecting drug release are well known to the skilled artisan and have been described in the art (Bamba et al., *Int. J. Pharm.*, 1979, 2, 307).

In another embodiment, enteric-coated preparations can be used for oral sustained release administration. Preferred coating materials include polymers with a pH-dependent solubility (i.e., pH-controlled release), polymers with a slow or pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release).

In still another embodiment, osmotic delivery systems are used for oral sustained release administration (Verma et al., *Drug Dev. Ind. Pharm.*, 2000, 26:695–708). In another embodiment, OROS™ osmotic devices are used for oral sustained release delivery devices (Theeuwes et al., U.S. Pat. No. 3,845,770; Theeuwes et al., U.S. Pat. No. 3,916,899).

In yet another embodiment, a controlled-release system can be placed in proximity of the target of the compounds and/or pharmaceutical composition of the invention, thus requiring only a fraction of the systemic dose (See, e.g., Goodson, in "Medical Applications of Controlled Release," supra, vol. 2, pp. 115–138 (1984)). Other controlled-release systems discussed in Langer, 1990, *Science* 249:1527–1533 may also be used.

5.7 Pharmaceutical Compositions of the Invention

The present pharmaceutical compositions contain a therapeutically effective amount of one or more compounds of the invention, preferably in purified form, together with a suitable amount of a pharmaceutically acceptable vehicle, so as to provide a form for proper administration to a patient. When administered to a patient, the compounds of the invention and pharmaceutically acceptable vehicles are preferably sterile. Water is a preferred vehicle when the compound of the invention is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present pharmaceutical compositions, if desired, can also contain minor amounts of wetting or emulsifying agents, or pH buffering agents. In addition, auxiliary, stabilizing, thickening, lubricating and coloring agents may be used.

Pharmaceutical compositions comprising a compound of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries, which facilitate processing of compounds of the invention into preparations that can be used pharmaceutically. Proper formulation is dependent upon the route of administration chosen.

The present pharmaceutical compositions can,take the form of solutions, suspensions, emulsion, tablets, pills, pellets, capsules, capsules containing liquids, powders, sustained-release formulations, suppositories, emulsions, aerosols, sprays, suspensions, or any other form suitable for use. In one embodiment, the pharmaceutically acceptable vehicle is a capsule (see e.g., Grosswald et al., U.S. Pat. No. 5,698,155). Other examples of suitable pharmaceutical vehicles have been described in the art (see Remington: The Science and Practice of Pharmacy, Philadelphia College of Pharmacy and Science, 20$^{th}$ Edition, 2000).

For topical administration a compound of the invention may be formulated as solutions, gels, ointments, creams, suspensions, etc. as is well-known in the art.

Systemic formulations include those designed for administration by injection, e.g., subcutaneous, intravenous, intramuscular, intrathecal or intraperitoneal injection, as well as those designed for transdermal, transmucosal, oral or pulmonary administration. Systemic formulations may be made in combination with a further active agent that improves mucociliary clearance of airway mucus or reduces mucous viscosity. These active agents include, but are not limited to, sodium channel blockers, antibiotics, N-acetyl cysteine, homocysteine and phospholipids.

In one embodiment, the compounds of the invention are formulated in accordance with routine procedures as a pharmaceutical composition adapted for intravenous administration to human beings. Typically, compounds of the invention for intravenous administration are solutions in sterile isotonic aqueous buffer. For injection, a compound of the invention may be formulated in aqueous solutions, preferably, in physiologically compatible buffers such as Hanks' solution, Ringer's solution, or physiological saline buffer. The solution may contain formulatory agents such as suspending, stabilizing and/or dispersing agents. When necessary, the pharmaceutical compositions may also include a solubilizing agent. Pharmaceutical compositions for intravenous administration may optionally include a local anesthetic such as lignocaine to ease pain at the site of the injection. Generally, the ingredients are supplied either separately or mixed together in unit dosage form, for example, as a lyophilized powder or water free concentrate in a hermetically sealed container such as an ampoule or sachette indicating the quantity of active agent. When the compound of the invention is administered by infusion, it can be dispensed, for example, with an infusion bottle containing sterile pharmaceutical grade water or saline. When the compound of the invention is administered by injection, an ampoule of sterile water for injection or saline can be provided so that the ingredients may be mixed prior to administration.

For transmucosal administration, penetrants appropriate to the barrier to be permeated are used in the formulation. Such penetrants are generally known in the art.

Pharmaceutical compositions for oral delivery may be in the form of tablets, lozenges, aqueous or oily suspensions, granules, powders, emulsions, capsules, syrups, or elixirs, for example. Orally administered pharmaceutical compositions may contain one or more optionally agents, for example, sweetening agents such as fructose, aspartame or saccharin; flavoring agents such as peppermint, oil of wintergreen, or cherry coloring agents and preserving agents, to provide a pharmaceutically palatable preparation. Moreover, where in tablet or pill form, the compositions may be coated to delay disintegration and absorption in the gastrointestinal tract, thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

For oral liquid preparations such as, for example, suspensions, elixirs and solutions, suitable carriers, excipients or diluents include water, saline, alkyleneglycols (e.g., propylene glycol), polyalkylene glycols (e.g., polyethylene glycol) oils, alcohols, slightly acidic buffers between pH 4 and pH 6 (e.g., acetate, citrate, ascorbate at between about 5.0 mM to about 50.0 mM) etc. Additionally, flavoring agents, preservatives, coloring agents, bile salts, acylcarnitines and the like may be added.

For buccal administration, the pharmaceutical compositions may take the form of tablets, lozenges, etc. formulated in conventional manner.

Liquid drug formulations suitable for use with nebulizers and liquid spray devices and EHD aerosol devices will typically include a compound of the invention with a pharmaceutically acceptable vehicle. Preferably, the pharmaceutically acceptable vehicle is a liquid such as alcohol, water, polyethylene glycol or a perfluorocarbon. Optionally, another material may be added to alter the aerosol properties of the solution or suspension of compounds of the invention. Preferably, this material is liquid such as an alcohol, glycol, polyglycol or a fatty acid. Other methods of formulating liquid drug solutions or suspension suitable for use in aerosol devices are known to those of skill in the art (see, e.g., Biesalski, U.S. Pat. No. 5,112,598; Biesalski, U.S. Pat. No. 5,556,611).

A compound of the invention may also be formulated in rectal or vaginal pharmaceutical compositions such as suppositories or retention enemas, e.g., containing conventional suppository bases such as cocoa butter or other glycerides.

In addition to the formulations described previously, a compound of the invention may also be formulated as a depot preparation. Such long acting formulations may be administered by implantation (for example, subcutaneously or intramuscularly) or by intramuscular injection. Thus, for example, a compound of the invention may be formulated with suitable polymeric or hydrophobic materials (for example, as an emulsion in an acceptable oil) or ion exchange resins, or as sparingly soluble derivatives, for example, as a sparingly soluble salt.

When a compound of the invention is acidic, it may be included in any of the above-described formulations as the free acid, a pharmaceutically acceptable salt, a solvate or a hydrate. Pharmaceutically acceptable salts substantially retain the activity of the free acid, may be prepared by reaction with bases and tend to be more soluble in aqueous and other protic solvents than the corresponding free acid form.

5.8 Therapeutic Doses

A compound of the invention, or pharmaceutical compositions thereof, will generally be used in an amount effective to achieve the intended purpose. For use to treat or prevent diseases or disorders characterized by aberrant vascularization, copper metabolism disorders, neurodegenerative disorders and obesity the compounds of structural Formula (I)

and/or pharmaceutical compositions thereof, are administered or applied in a therapeutically effective amount.

The amount of a compound of the invention that will be effective in the treatment of a particular disorder or condition disclosed herein will depend on the nature of the disorder or condition, and can be determined by standard clinical techniques known in the art as previously described. In addition, in vitro or in vivo assays may optionally be employed to help identify optimal dosage ranges. The amount of a compound of the invention administered will, of course, be dependent on, among other factors, the subject being treated, the weight of the subject, the severity of the affliction, the manner of administration and the judgment of the prescribing physician.

For example, the dosage may be delivered in a pharmaceutical composition by a single administration, by multiple applications or controlled release. In one embodiment, the compounds of the invention are delivered by oral sustained release administration. Preferably, in this embodiment, the compounds of the invention are administered twice per day (more preferably, once per day). Dosing may be repeated intermittently, may be provided alone or in combination with other drugs and may continue as long as required for effective treatment of the disease state or disorder.

Suitable dosage ranges for oral administration depend on the potency of the drug, but are generally between about 0.001 mg to about 200 mg of a compound of the invention per kilogram body weight. Dosage ranges may be readily determined by methods known to the artisan of ordinary skill.

Suitable dosage ranges for intravenous (i.v.) administration are about 0.01 mg to about 100 mg per kilogram body weight. Suitable dosage ranges for intranasal administration are generally about 0.01 mg/kg body weight to about 1 mg/kg body weight. Suppositories generally contain about 0.01 milligram to about 50 milligrams of a compound of the invention per kilogram body weight and comprise active ingredient in the range of about 0.5% to about 10% by weight. Recommended dosages for intradermal, intramuscular, intraperitoneal, subcutaneous, epidural, sublingual or intracerebral administration are in the range of about 0.001 mg to about 200 mg per kilogram of body weight. Effective doses may be extrapolated from dose-response curves derived from in vitro or animal model test systems. Such animal models and systems are well-known in the art.

The compounds of the invention are preferably assayed in vitro and in vivo, for the desired therapeutic or prophylactic activity, prior to use in humans. For example, in vitro assays can be used to determine whether administration of a specific compound of the invention or a combination of compounds of the invention is preferred for reducing convulsion. The compounds of the invention may also be demonstrated to be effective and safe using animal model systems.

Preferably, a therapeutically effective dose of a compound of the invention described herein will provide therapeutic benefit without causing substantial toxicity. Toxicity of compounds of the invention may be determined using standard pharmaceutical procedures and may be readily ascertained by the skilled artisan. The dose ratio between toxic and therapeutic effect is the therapeutic index. A compound of the invention will preferably exhibit particularly high therapeutic indices in treating disease and disorders. The dosage of a compound of the inventions described herein will preferably be within a range of circulating concentrations that include an effective dose with little or no toxicity.

5.9 Combination Therapy

In certain embodiments of the present invention, the compounds and/or pharmaceutical compositions of the invention can be used in combination therapy with at least one other therapeutic agent. The compound and/or pharmaceutical composition of the invention and the therapeutic agent can act additively or, more preferably, synergistically. In a preferred embodiment, a compound of the invention or a pharmaceutical composition of a compound of the invention is administered concurrently with the administration of another therapeutic agent, which may be part of the same pharmaceutical composition as the compound of the invention or a different pharmaceutical composition. In another embodiment, a pharmaceutical composition of a compound of the invention is administered prior or subsequent to administration of another therapeutic agent.

In particular, in one preferred embodiment, the compounds and/or pharmaceutical compositions of the invention can be used in combination therapy with other chemotherapeutic agents (e.g., alkylating agents (e.g., nitrogen mustards (e.g., cyclophosphamide, ifosfamide, mechlorethamine, melphalen, chlorambucil, hexamethylmelamine, thiotepa), alkyl sulfonates (e.g., busulfan), nitrosoureas, triazines) antimetabolites (e.g., folic acid analogs, pyrimidine analogs (e.g., fluorouracil, floxuridine, cytosine arabinoside, etc.), purine analogs (e.g., mercaptopurine, thiogunaine, pentostatin, etc.), natural products (e.g., vinblastine, vincristine, etoposide, tertiposide, dactinomycin, daunorubicin, doxurubicin, bleomycin, mithrmycin, mitomycin C, L-asparaginase, interferon alpha), platinum coordination complexes (e.g., cis-platinum, carboplatin, etc.), mitoxantrone, hydroxyurea, procarbazine, hormones and antagonists (e.g., prednisone, hydroxyprogesterone caproate, medroxyprogesterone acetate, megestrol acetate, diethylstilbestrol, ethinyl estradiol, tamoxifen, testosterone propionate, fluoxymesterone, flutamide, leuprolide, etc.), anti-angiogenesis agents or inhibitors (e.g., angiostatin, retinoic acids and paclitaxel, estradiol derivatives, thiazolopyrimidine derivatives, etc.), apoptosis-inducing agents (e.g., antisense nucleotides that block oncogenes which inhibit apoptosis, tumor suppressors, TRAIL, TRAIL polypeptide, Fas-associated factor 1, interleukin-1β-converting enzyme, phosphotyrosine inhibitors, RXR retinoid receptor agonists, carbostyril derivatives, etc.), chelators (penicillamine, zinc, trientine, etc.) and other anti-obesity agents.

5.10 Therapeutic Kits

The current invention provides therapeutic kits comprising the compounds of the invention or pharmaceutical compositions of the invention. The therapeutic kits may also contain other compounds (e.g., chemotherapeutic agents, natural products, hormones or antagonists, anti-angiogenesis agents or inhibitors, apoptosis-inducing agents or chelators) or pharmaceutical compositions of these other compounds.

Therapeutic kits may have a single containers which contains the compound of the invention or pharmaceutical compositions of the invention with or without other components (e.g., other compounds or pharmaceutical compositions of these other compounds) or may have distinct container for each component. Preferably, therapeutic kits of the invention include a compound of the invention or a pharmaceutical composition of the invention packaged for use in combination with the co-administration of a second compound (preferably, a chemotherapeutic agent, a natural product, a hormone or antagonist, a anti-angiogenesis agent or inhibitor, a apoptosis-inducing agent or a chelator) or a pharmaceutical composition thereof. The components of the kit may be pre-complexed or each component may be in a separate distinct container prior to administration to a patient.

The components of the kit may be provided in one or more liquid solutions, preferably, an aqueous solution, more preferably, a sterile aqueous solution. The components of the kit may also be provided as solids, which may be converted into liquids by addition of suitable solvents, which are preferably provided in another distinct container.

The container of a therapeutic kit may be a vial, test tube, flask, bottle, syringe, or any other means of enclosing a solid or liquid. Usually, when there is more than one component, the kit will contain a second vial or other container, which allows for separate dosing. The kit may also contain another container for a pharmaceutically acceptable liquid.

Preferably, a therapeutic kit will contain apparatus (e.g., one or more needles, syringes, eye droppers, pipette, etc.), which enables administration of the components of the kit.

6. EXAMPLES

The invention is further defined by reference to the following examples, which describe in detail, preparation of compounds of the invention and methods for assaying for biological activity. It will be apparent to those skilled in the art that many modifications, both to materials and methods, may be practiced without departing from the scope of the invention.

6.1 Example 1

General Procedure for Synthesis of Tetrathiomolybdate Derivatives

The commercially available aqueous solution of quaternary ammonium hydroxide (2 eq.) was added to ammonium tetrathiomolybdate (1 eq.) followed by deionized water until all the solid material was dissolved. The solution was placed on a rotary evaporator under vacuum (ca. 5–10 torr) at 20° C. for 2 hours and water was replaced as needed to maintain a constant volume. If this procedure resulted in a precipitate, the solid was collected by filtration, washed with isopropanol, ethanol, and diethyl ether, and then dried under high vacuum for 24 hours in a vacuum desiccator in the presence of $P_2O_5$. If the solution remained clear, the reaction mixture was first filtered to remove small amounts of solid impurities, and the product was precipitated from the filtrate with isopropanol. The solid was collected by filtration, washed with isopropanol, ethanol, and diethyl ether and then dried under high vacuum for 24 hours in a vacuum desiccator in the presence of $P_2O_5$.

6.2 Example 2

General Procedure for Synthesis of Tetrathiomolybdate Derivatives

The solid quaternary ammonium halide (2 eq.) was added to a suspension of ammonium tetrathiomolybdate (1 eq.) in dry acetonitrile (5 mL per mmol of TM) and the resulting mixture was stirred at room temperature under nitrogen for 18 hours. If this procedure resulted in a precipitate, the solid was collected by filtration, washed with water, isopropanol, ethanol and diethyl ether, and then dried under high vacuum for 24 hours in a vacuum desiccator in the presence of $P_2O_5$. If the solution remained clear, the reaction mixture was first filtered, and the filtrate was concentrated in vacuo. The resulting solid was suspended in water and filtered, and the solid was washed with isopropanol, ethanol and diethyl ether and then dried under high vacuum for 24 hours in a vacuum desiccator in the presence of $P_2O_5$.

6.3 Example 3

Tetrathiomolybdate, bis(triethylmethyl ammonium)

This compound was prepared from ammonium tetrathiomolybdate (994 mg, 3.82 mmol) and a 20% by weight aqueous solution of triethylmethylammonium hydroxide (5.12 g, 7.69 mmol) according to the procedure of Example 1 and provided 1.05 g (60%) of the title compound as an orange-red solid. IR (KBr, $cm^{-1}$) 472; $^1$H NMR (300 MHz, DMSO-d6) δ 3.27 (q, J=7.3 Hz, 12H), 2.89 (s, 6H), 1.19 (tt, J=7.3, 1.8 Hz, 18H); $^{13}$C NMR (75 MHz, DMSO-d6) δ 55.1 (6C), 46.1 (2C), 7.7 (6C); ES MS m/z (triethylmethyl ammonium)$^+$ 116.3; UV ($H_2O$) 468 nm (ε=12000). Analysis: Calcd for $C_{14}H_{36}MoN_2S_4$: C, 36.82; H, 7.95; N, 6.13. Found: C, 37.07; H, 7.88; N, 6.24.

6.4 Example 4

Tetrathiomolybdate, bis(triethylphenyl ammonium)

This compound was prepared from ammonium tetrathiomolybdate (1.00 g, 3.85 mmol) and a 10% by weight aqueous solution of triethylphenylammonium hydroxide (15.1 g, 7.71 mmol) according to the procedure of Example 1, and provided 388 mg (17%) of the title compound as an orange solid. IR (KBr, $cm^{-1}$) 470; $^1$H NMR (300 MHz, DMSO-d6) δ 7.91 (d, J=8.2 Hz, 4H), 7.69–7.55 (m, 6H), 3.89 (q, J=6.9 Hz, 12H), 1.04 (t, J=6.9 Hz, 18H); $^{13}$C NMR (75 MHz, DMSO-d6) δ 141.9 (2C), 130.5 (4C), 130.1 (2C), 122.7 (4C), 55.3 (6C), 8.0 (6C); ES MS m/z (triethylphenyl ammonium)$^+$ 178.2; UV ($H_2O$) 468 nm (ε=12300). Analysis: Calcd for $C_{24}H_{40}MoN_2S_4$: C, 49.63; H, 6.94; N, 4.82; S, 22.08. Found: C, 49.39; H, 7.23; N, 5.15; S, 22.41.

6.5 Example 5

Tetrathiomolybdate, bis(choline)

In the instant application, bis(choline) tetrathiomolybdate has the same chemical structure as bis[2-hydroxyethyl) trimethyl ammonium] tetrathiomolybdate. This compound was prepared from ammonium tetrathiomolybdate (1.08 g, 4.15 mmol) and a 50% by weight aqueous solution of choline hydroxide (2.01 g, 8.29 mmol) according to the procedure of Example 1 and afforded 1.30 g (73%) of the title compound as an orange solid. IR (KBr, $cm^{-1}$) 3389, 474; $^1$H NMR (300 MHz, DMSO-d6) δ 5.21 (t, J=4.6 Hz, 2H), 3.87–3.79 (m, 4H), 3.43 (t, J=4.6 Hz, 4H), 3.13 (s, 18H); $^{13}$C NMR (75 MHz, DMSO-d6) δ 67.1 (2C), 55.5 (2C), 53.3 (6C); ES MS m/z (choline)$^+$ 104.2; UV ($H_2O$) 468 nm (ε=12900). Analysis: Calcd for $C_{10}H_{28}MoN_2O_2S_4$: C, 27.77; H, 6.52; N, 6.48; S, 29.65; Mo, 22.18. Found: C, 27.63; H, 6.84; N, 6.39; S, 29.86; Mo, 22.23.

6.6 Example 6

Tetrathiomolybdate, bis(acetylcholine)

This compound was prepared from acetylcholine chloride (732 mg, 4.03 mmol) and ammonium tetrathiomolybdate (500 mg, 1.92 mmol) according to the procedure of Example 2, and afforded 390 mg (39%) of the title compound as an orange-red solid. IR (KBr, cm$^{-1}$) 1747, 1728, 482, 469, 461; $^1$H NMR (300 MHz, DMSO-d6) δ 4.47–4.41 (m, 4H), 3.72–3.69 (m, 4H), 3.16 (s, 18H), 2.07 (s, 6H); $^{13}$C NMR (75 MHz, DMSO-d6) δ 170.1 (2C), 63.9 (2C), 58.0 (2C), 53.1 (6C), 20.9 (2C); ES MS m/z (acetylcholine)$^+$ 146.4; UV (H$_2$O) 468 nm (ε=13300). Analysis: Calcd for C$_{14}$H$_{32}$MoN$_2$O$_4$S$_4$: C, 32.55; H, 6.24; N, 5.42; S, 24.82. Found: C, 32.66; H, 6.23; N, 5.51; S, 24.97.

6.7 Example 7

Tetrathiomolybdate, bis[2-(methoxy)ethyltrimethyl ammonium]

This compound was prepared from ammonium tetrathiomolybdate (5 g, 19.2 mmol) and 2-(methoxy)ethyltrimethylammonium chloride (6.199 g, 40.3 mmol, see below in this example for synthesis) in a stirring suspension of acetonitrile (125 ml). The suspension was stirred for 2 hours, during which time a fine light red powder formed. The precipitate was filtered over a glass frit, and the acetonitrile was evaporated to afford 1.76 g (20%) of the title compound that was dried in a vacuum. Analysis: Calcd for C$_{14}$H$_{32}$MoN$_2$O$_4$S$_4$: C, 31.293; H, 7.003; N, 6.082. Found: C, 30.85; H, 6.89; N, 6.11.

The 2-(methoxy)ethyltrimethylammonium chloride was prepared by combining 1-chloro-2-methoxyethane (3.636 g, 38.5 mmol, see below in this example for synthesis) in a 25 ml round bottom flask with trimethyl amine (40% in water, 7.77 ml, 50 mmol). The mixture was heated at reflux for 24 hours, cooled to room temperature, and washed three times with 15 ml diethyl ether. The solvent was evaporated from the aqueous layer leaving a clumpy white solid that was washed with isopropanol and dried under vacuum to afford 4.136 g (70%) of the compound.

The 1-chloro-2-methoxyethane was prepared by combining 20 ml of chloroform with 2-methoxyethanol (5.4 ml, 69 mmol) in a nitrogen atmosphere. Thionyl chloride (5.0 ml, 69 mmol) and pyridine (5.5 ml, 69 mmol) were added sequentially by syringe, stirred at room temperature for 1 hour, and refluxed for 1 additional hour. The reaction components were cooled, quenched with water, washed twice with 25 ml 1 M HCl, and the solvent was evaporated. The reaction products were filtered over silica gel and eluted with acetone to afford 5.94 g (91%) of the light brown component.

The mechanism for the synthesis of bis[2-(methoxy) ethyltrimethylammonium] tetrathiomolybdate according to the present example, is as follows:

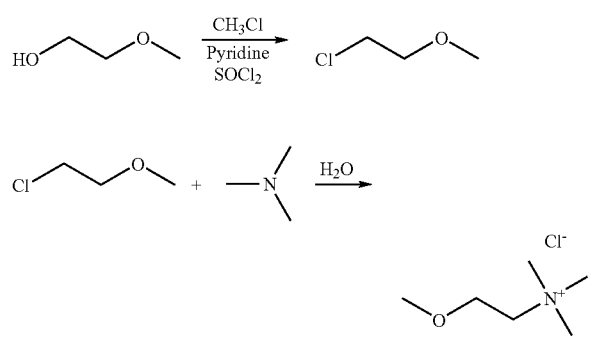

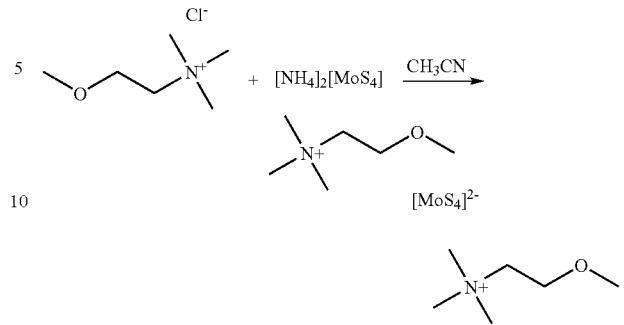

6.8 Example 8

Tetrathiomolybdate, bis[alkyldimethyl(phenylmethyl) ammonium]

This compound was prepared from ammonium tetrathiomolybdate (1.00 g, 3.84 mmol) and benzalkonium chloride (2.90 g, 8.07 mmol) according to the procedure of Example 6 and afforded 2.75 g (82%) of the title compound as a thick, red oil. IR (film, cm$^{-1}$) 471; $^1$H NMR (300 MHz, DMSO-d6) δ 7.58–7.46 (m, 10H), 4.54 (s, 4H), 3.24–3.20 (m, 4H), 2.95 (s, 12H), 1.83–1.71 (m, 4H), 1.30–1.21 (m, 40H), 0.88–0.81 (m, 6H); ES MS m/z [dodecyldimethyl(phenylmethyl) ammonium]$^+$ 304.7, [tetradecyldimethyl(phenylmethyl) ammonium]$^+$ 332.7; UV (DMSO) 473.5 nm (ε=10100).

6.9 Example 9

Tetrathiomolybdate, Bis(1-ethyl-3-methyl-1H-imidazolium)

This compound was prepared from tetrathiomolybdate, bis(ammonium) (1.00 g, 3.84 mmol) and 1-ethyl-3-methyl-1H-imidazolium chloride (1.18 g, 8.06 mmol) according to the procedure of Example 2 with the following modifications; the mixture was filtered and the filtrate was concentrated in vacuo and the resulting solids were filtered, rinsed with EtOH, and ethyl ether and dried in a high vacuum desiccator for 24 hr giving the title compound (0.419 g, 24%) as a reddish-brown solid. IR (KBr pellet, cm$^{-1}$) 3064, 1566, 1167, 465; $^1$H NMR (300 MHz, DMSO-d$_6$) δ 9.24 (s, 1 H), 7.77 (s, 1 H), 7.69 (s, 1 H), 4.20 (q, J=7.3 Hz), 3.86 (s, 3 H), 1.40 (t, J=7.3 Hz); $^{13}$C NMR (75 MHz, DMSO-d$_6$) δ 136.9, 123.5, 121.8, 44.1, 35.7, 15.3; MS m/z (C$_6$H$_{11}$N$_2$)$^+$ 111.2; UV (H$_2$O) 468nm (ε=11016). Analysis: Calcd for C$_{12}$H$_{22}$N$_4$ MoS$_4$: C, 32.28; H, 4.97; N, 12.55; S, 28.72. Found: C, 31.88; H, 4.87; N, 12.56; S, 28.79.

6.10 Example 10

Tetrathiomolybdate, bis(phenyltrimethylammonium)

This compound was prepared from tetrathiomolybdate, bis(ammonium) (1.00 g, 3.84 mmol) and phenyltrimethylammonium chloride (1.38 g, 8.06 mmol) according to the procedure of Example 2, and provided the title compound (0.859 g, 45%) as an orange solid. IR (KBr pellet, cm$^{-1}$) 3032, 3005, 1485, 1458, 473; $^1$H NMR (300 MHz, DMSO-d$_6$) δ 7.98 (m, 4 H), 7.61 (m, 6 H), 3.62 (s, 18 H); $^{13}$C NMR (75 MHz, DMSO-d$_6$) δ147.2, 130.0, 129.9, 120.5, 56.3; MS m/z ($C_9H_{14}N$)$^+$ 136.2; UV ($H_2O$) 468 nm ($\epsilon$=12900). Analysis: Calcd for $C_{18}H_{28}N_2MoS_4$: C, 43.53; H, 5.68; N, 5.64; S, 25.83. Found: C, 43.66; H, 5.98; N, 5.76; S, 25.73.

6.11 Example 11

Tetrathiomolybdate, bis(benzyltrimethylammonium)

This compound was prepared from tetrathiomolybdate, bis(ammonium) (0.500 g, 1.92 mmol) and benzyltrimethylammonium hydroxide (1.60 g of a 40% aqueous solution, 3.84 mmol) according to the procedure of Example 1, providing the title compound (0.869 g, 91%) as a red solid. Mp 179–181° C. (decomp); IR (KBr pellet, cm$^{-1}$) 2995, 1483, 1454, 474; $^1$H NMR (300 MHz, DMSO-$d_6$) δ 7.52 (m, 10 H), 4.56 (s, 4 H), 3.04 (s 18 H); $^{13}$C NMR (75 MHz, DMSO-$d_6$) δ 132.9, 130.2, 128.9, 128.4, 67.7, 51.7; MS m/z ($C_{10}H_{16}N$)$^+$ 150.3; UV (H2O) 468 nm ($\epsilon$=12008). Analysis: Calcd for $C_{20}H_{32}N_2MoS_4$: C, 45.78; H, 6.15; N, 5.34; S, 24.44. Found: C, 45.67; H, 6.15; N, 5.62; S, 24.41.

6.12 Example 12

Tetrathiomolybdate, Pentane-1,5-bis(trimethylammonium)

To a suspension of tetrathiomolybdate, bis(ammonium) (0.100 g, 0.226 mmol) in $CH_3CN$ (2 mL) was added a solution of pentane-1,5-bis(trimethyl ammonium) iodide (0.054 g, 0.205 mmol) dissolved in water (2 mL). After stirring for 5 hours at room temperature, the brownish-red solids were filtered, suspended in water then refiltered and washed with EtOH, iPrOH and $Et_2O$. After drying in a high-vacuum desiccator overnight a red solid was obtained giving the title compound (0.051 g, 60 %). IR (KBr pellet, cm$^{-1}$) 2997, 472; $^1$H NMR (300 MHz, MeOH-$d_5$) δ 3.22 (m, 4 H), 2.98 (s 18 H), 1.70 (m, 4 H), 1.31 (2 H); $^{13}$C NMR (75 MHz, DMSO-$d_6$) δ 79.4, 64.9, 52.2, 21.6; UV ($H_2O$) 468 nm ($\epsilon$=12025). Analysis: Calcd for $C_{11}H_{28}N_2MoS_4$: C, 32.03; H, 6.84; N, 6.79; S, 31.09. Found: C, 32.40; H, 6.74; N, 6.80; S, 30.87.

6.13 Example 13

Tetrathiomolybdate, bis(2-hydroxyiminomethyl-1-methyl-pyridinium)

This compound was prepared from tetrathiomolybdate, bis(ammonium) (1.00 g, 3.84 mmol) and 2-hydroxyiminomethyl-1-methyl-pyridinium chloride (1.39 g, 8.06 mmol) according to the procedure of Example 2 with the following modification: water (10 mL) was added to dissolve the ammonium halide. The title compound (1.20 g, 66%) was provided as a red solid. IR (KBr pellet, cm$^{-1}$) 1002, 477; $^1$H NMR (300 MHz, DMSO-$d_6$) δ 9.05 (app d, 1 H), 8.67 (s, 1 H), 8.54 (app t, 1 H), 8.08 (app d, 1 H), 8.04 (app t, 1 H), 4.39 (s, 3 H); $^{13}$C NMR (75 MHz, DMSO-$d_6$) δ 147.6, 147.1, 145.1, 142.0, 127.4, 124.9, 46.3; MS m/z ($C_7H_9N_2O$)$^+$ 137.1; UV ($H_2O$) 468 nm ($\epsilon$=12092).

6.14 Example 14

Tetrathiomolybdate, bis(11-dimethylpyrrolidinium)

This compound was prepared from ammonium tetrathiomolybdate (0.644 g, 2.47 mmol) and 1,1-dimethylpyrrolidinium iodide (1.18 g, 5.19 mmol) according to the procedure of Example 2, and provided an orange solid. IR (KBr, cm$^{-1}$) 471; $^1$H NMR (300 MHz, DMSO-d6) δ 2.09 (m, 4H), 3.10 (s, 6H), 3.47 (t, J=6 Hz, 4H); $^{13}$C (75 MHz, DMSO-d6) δ 21.44, 50.86, 64.68; ES MS m/z (1,1-dimethylpyrrolidinium)$^+$ 100; UV ($H_2O$) 468 nm ($\epsilon$=14130). Analysis: Calcd for $C_{12}H_{28}N_2MoS_4$: C, 33.94; H, 6.64; N, 6.59; S, 30.21. Found: C, 33.68; H, 6.97; N, 6.58; S, 30.06.

6.15 Example 15

Tetrathiomolybdate, ethylene bis ammonium

Ammonium chloride (0.411 g, 7.68 mmol) and ethylene diamine (0.230 g, 3.84 mmol) were dissolved in 50 mL of water. To this solution was added ammonium tetrathiomolybdate (1.0 g, 3.84 mmol) and the mixture was stirred for 3 hours. The brick red solid that formed was collected by filtration (233 mg), rinsed with isopropanol and $Et_2O$ and dried under high vacuum for 24 hours in a vacuum desiccator in the presence of $P_2O_5$. The mother liquors were concentrated to ~⅓ their original volume and the newly formed crystals were again collected by filtration and rinsed (387 mg). Total recovery of the title compound was 620 mg, (56.8%). IR (KBr, cm$^{-1}$) 474; $^1$H NMR (300 MHz, DMSO-d6) δ 3.08 (s, 4H); 7.79 (br s, 4H); $^{13}$C (75 MHz, DMSO-d6) δ 37.08; ES MS m/z (ethylene bis ammonium)$^+$ 60.5; UV ($H_2O$) 468 nm ($\epsilon$=12310). Analysis: Calcd for $C_2H_{10}MoN_2S_4$: C, 8.39; H, 3.52; N, 9.78; S, 44.80. Found: C, 8.75; H, 3.28; N, 10.05; S, 44.99.

6.16 Example 16

Tetrathiomolybdate, bis(1,4-dimethylpyridinium)

This compound was prepared from ammonium tetrathiomolybdate (0.50g, 1.92 mmol) and 1,4-dimethyl pyridinium iodide (0.95 g, 4.03 mmol) according to the procedure of Example 2 and provided 203 mg (24%) of the title compound as an orange solid. IR (KBr, cm$^{-1}$) 469; $^1$H NMR (300 MHz, DMSO-d6) δ 2.49 (s, 3H), 4.30 (s, 3H), 7.93, (d, J=6 Hz, 2H), 8.85 (d, J=6 Hz, 2H); $^{13}$C (75 MHz, DMSO-d6) δ 21.31, 47.03, 127.94 (2C), 144.77, 157.93; ES MS m/z bis(1,4-dimethylpyridinium)$^+$ 108.2; UV ($H_2O$) 468 nm ($\epsilon$=13480). Analysis: Calcd for $C_{14}H_{20}N_2MoS_4$: C, 38.17; H, 4.57; N, 6.35; S. 29.11. Found: C, 38.27; H, 4.24; N, 6.36; S, 28.89.

6.17 Example 17

Tetrathiomolybdate, bis(phenyltrimethyl ammonium)

This compound was prepared according to the procedure of Example 1. IR (cm–1) 470; $^1$H NMR (400 MHz, DMSO-d6) δ 7.99–7.97 (d, J=8.4 Hz, 4H), 7.66–7.56 (m, 6H), 3.62 (s, 18H); UV ($H_2O$) 468 nm ($\epsilon$=13151). Analysis: Calcd for $C_{18}H_{28}MoN_2S_4$: C, 43.53; H, 5.68; N, 5.64; S, 25.83. Found: C, 42.72; H, 5.20; N, 5.27; S, 27.54.

6.18 Example 18

Tetrathiomolybdate, bis(vinyltrimethyl ammonium)

This compound was prepared according to the procedure of Example 1. IR (cm–1) 470; $^1$H NMR (400 MHz, DMSO-d6) δ 6.62–6.56 (m, 2H), 5.76 (d, J=15.2 Hz, 2H), 5.54 (m, 2H), 3.24 (s, 18H); UV ($H_2O$) 468 nm ($\epsilon$=18012).

6.19 Example 19

Tetrathiomolybdate, bis(cyclopropylmethyltrimethyl ammonium)

This compound was prepared according to the procedure of Example 2. IR (cm−1) 474; $^1$H NMR (400 MHz, DMSO-d6) δ 3.24 (d, J=7.2 Hz, 4H), 3.11 (s, 18H), 1.16 (m, 2H), 0.72–0.69 (m, 4H), 0.42–0.38 (m, 4H); UV (H2O) 468 nm (ε=14239).

6.20 Example 20

Tetrathiomolybdate, bis(benzylphenyldimethylammonium)

This compound was prepared according to the procedure of Example 2. IR (cm$^{-1}$) 470; $^1$H NMR (400 MHz, DMSO-d6) δ 7.76–6.60 (m), 5.00 (s), 2.87 (s); UV (H$_2$O) 468 nm (ε=15606).

6.21 Example 21

Tetrathiomolybdate, hexane-1,6-bis(trimethyl ammonium)

This compound was prepared according to the procedure of Example 2. IR (cm$^{-1}$) 478; UV (DMSO) 468 nm (ε=12666).

6.22 Example 22

Tetrathiomolybdate, bis[(2-hydroxyethyl)trimethyl ammonium]

Choline hydroxide (50% w/w in water, 2.56 mL, 11.3 mmol) was added to a solution of ammonium molybdate tetrahydrate (1.0 g, 5.66 mmol of Mo) in 2.5 mL of deionized water. Hydrogen sulfide gas was bubbled through the solution for 50 minutes at room temperature, during which time the color of the solution turned from brown to red. Nitrogen gas was bubbled through the solution for 10 min to purge the reaction mixture of dissolved hydrogen sulfide and the solvent was removed under reduced pressure. The red solid was dissolved in deionized water (3×25 mL) and the solvent was removed repeatedly under reduced pressure to remove dissolved ammonia. The crude product was dissolved in 20 mL of deionized water and filtered. The product was precipitated by addition of isopropanol to the aqueous layer. The solids were collected by filtration and washed with ethanol (3x) and diethyl ether (3x) to produce the crude title compound (2.218 g, 90%). Recrystallization from deionized water and isopropanol, and washing with ethanol (3x) and diethyl ether (3x) afforded the title compound (1.565 g, 62%) as plate-like red crystals: $^1$H NMR (300 MHz, DMSO-d$_6$) δ 5.23 (br t, J=4.7 Hz, 2H), 3.85 (br s, 4H), 3.46–3.43 (m, 4H), 3.14 (s, 18H).

6.23 Example 23

Tetrathiomolybdate, bis[(2-hydroxyethyl)trimethyl ammonium]

Hydrogen sulfide gas was bubbled through a solution of choline hydroxide (50% w/w in water, 5.2 mL, 23 mmol) and ammonium hydroxide (30% w/w in water, 8.2 mL, 70 mmol) in a tared pressure vessel for six minutes. The amount of hydrogen sulfide dissolved in the solution was 2.5 g. Ammonium molybdate tetrahydrate (2.01 g, 11.4 mmol) dissolved in deionized water (2.5 mL) was added to the pressure vessel and the sides washed with deionized water (0.5 mL). The reaction mixture was sealed and stirred at room temperature for 2 hours and 45 minutes, during which time crystals formed in the red solution. The mixture was transferred to a round-bottomed flask and deionized water added until the solid dissolved. The solvent was removed under reduced pressure, the residue taken up in deionized water, and the concentration step repeated. The resulting red residue was recrystallized from deionized water and isopropanol and the red plates washed once with isopropanol, once with ethanol, once with diethyl ether, and dried in a vacuum desiccator in the presence of phosphorus pentoxide for 23 hours to afford 3.05 g (62%) of the title compound. $^1$H NMR (300 MHz, DMSO-d6) δ 5.21 (t, J=4.6 Hz, 2H), 3.87–3.79 (m, 4H), 3.43 (t, J=4.6 Hz, 4H), 3.13 (s, 18H); $^{13}$C NMR (75 MHz, DMSO-d$_6$) δ 67.1 (2C), 55.5 (2C), 53.3 (6C); MS m/z (choline)$^+$ 104.2; UV (H$_2$O) 468 nm (ε=12400). Analysis: Calcd for $C_{10}H_{28}MoN_2O_2S_4$: C, 27.77; H, 6.52; N, 6.48; S, 29.65. Found: C, 27.76; H, 6.59; N, 6.85; S, 29.52.

6.24 Example 24

Tetrathiomolybdate, bis[(2-hydroxyethyl)trimethyl ammonium]

Deionized water (200 mL) was added to choline hydroxide (50% w/w in water, 38.2 mL, 14.7 mmol), followed by ammonium tetrathiomolybdate (19.1 g, 7.35 mmol) and the flask swirled until all the solid material was dissolved. The solution was placed on a rotary evaporator under vacuum (ca. 5–10 torr) with the bath at 20° C. for 110 minutes and the water was replaced as needed to maintain a constant volume. The reaction mixture was filtered to remove small amounts of solid impurities, and the product was precipitated from the filtrate with isopropanol (1 L). The solid was collected by filtration, washed with isopropanol, ethanol, and diethyl ether and then dried under high vacuum for 21 hours to afford 28.32 g (89%) of the desired product as an orange powder. The crude product was recrystallized from deionized water and isopropanol to afford red plates, which were washed once with isopropanol, once with ethanol, once with diethyl ether, and dried in a vacuum desiccator in the presence of phosphorus pentoxide for 24 hours to afford 20.76 g (65%) the title compound. $^1$H NMR (300 MHz, DMSO-d$_6$) δ 5.23 (t, J=4.8 Hz, 2H), 3.89–3.81 (m, 4H), 3.44 (t, J=4.8 Hz, 4H), 3.14 (s, 18H). Analysis: Calcd for $C_{10}H_{28}MoN_2O_2S_4$: C, 27.77; H, 6.52; N, 6.48; S, 29.65. Found: C, 27.91; H, 6.21; N, 6.26; S, 29.70.

6.25 Example 25

Tetrathiomolybdate, Bis[(2-hydroxyethyl)trimethyl ammonium]

In a 500 mL Erlenmeyer flask, [NH$_4$]$_2$[MoS$_4$] (100 g, 0.380 mol) was suspended in 200 mL of distilled water. To the suspension was added a 45 wt % solution of choline hydroxide in methanol (250 mL) (commercially available). Upon addition, a large amount of a bright red precipitate formed. Under a stream of nitrogen the suspension was heated to 40° C. with vigorous stirring until all solids dissolved (~1 hour). The deep red solution was kept under reduced pressure for 4 hours, during which time a red crystalline solid precipitated. The suspension was cooled in an ice bath for 30 minutes and then filtered. The product was washed with isopropyl alcohol until the washings were clear, then washed with diethyl ether and finally dried under vacuum to give 138 g of highly crystalline product (83% yield).

6.26 Example 26

X-Ray Structure Determination of Choline Tetrathiomolybdate

Diffraction data for a red crystal of $(Choline)_2MoS_4$ were collected at 158(2) K using a Siemens SMART area diffractometer (Siemens AG, Wittelsbacherplatz 2, D-80333, Munich, Federal Republic of Germany). A monoclinic P lattice was obtained with a cell: a=18.6066(1), b=12.7061(1), c=17.7621(2), and β=117.540(1) (Space group $P2_1/c$). The crystal structure was solved by direct methods and shows 2 $[MOS_4]$ and 4 choline cations in the asymmetric unit. After least squares refinement of all non-hydrogen atoms in the unit cell and convergence the final R factor was 0.06. The cell coordinates of the atoms in the unit cell are as follows:

| Atom | x/a | y/b | z/c |
| --- | --- | --- | --- |
| Mo1 | 0.3502 | 0.7432 | 0.4307 |
| Mo2 | 0.1641 | 0.2579 | 0.0786 |
| N1 | 0.4724 | 0.6022 | 0.2250 |
| N2 | 0.3306 | 0.3142 | 0.4043 |
| N3 | −0.0120 | 0.0317 | −0.3170 |
| N4 | 0.1920 | 0.8572 | 0.1184 |
| S1 | 0.2450 | 0.8268 | 0.4246 |
| S2 | 0.4354 | 0.8566 | 0.4245 |
| S3 | 0.4096 | 0.6553 | 0.5492 |
| S4 | 0.3114 | 0.6324 | 0.3236 |
| S5 | 0.2769 | 0.1760 | 0.1066 |
| S6 | 0.1167 | 0.1908 | 0.1604 |
| S7 | 0.0768 | 0.2372 | −.0535 |
| S8 | 0.1883 | 0.4248 | 0.1079 |
| O1 | 0.6860 | 0.9215 | 0.6690 |
| O2 | 0.6133 | 0.6075 | 0.8536 |
| O3 | 0.8951 | 0.3408 | 0.7335 |
| O4 | 0.9355 | 0.3376 | 0.5362 |
| C1 | 0.7156 | 0.8812 | 0.6189 |
| C2 | 0.6576 | 0.7959 | 0.5590 |
| C3 | 0.6471 | 0.6801 | 0.6669 |
| C4 | 0.7534 | 0.6488 | 0.6274 |
| C5 | 0.6139 | 0.6151 | 0.5265 |
| C6 | 0.6288 | 0.5111 | 0.8973 |
| C7 | 0.6144 | 0.4157 | 0.8417 |
| C8 | 0.5016 | 0.4766 | 0.7046 |
| C9 | 0.5221 | 0.2904 | 0.7373 |
| C10 | 0.4710 | 0.4023 | 0.8135 |
| C11 | 0.9086 | 0.4169 | 0.7986 |
| C12 | 0.9240 | 0.5165 | 0.7797 |
| C13 | 1.0580 | 0.4580 | 0.7905 |
| C14 | 1.0186 | 0.6375 | 0.7813 |
| C15 | 1.0496 | 0.5430 | 0.9103 |
| C16 | 0.9086 | 0.4815 | 0.5675 |
| C17 | 0.8505 | 0.4262 | 0.4598 |
| C18 | 0.7199 | 0.3849 | 0.3353 |
| C19 | 0.8417 | 0.3763 | 0.3214 |
| C20 | 0.8182 | 0.2446 | 0.4035 |

6.27 Example 27

Chemical Stability Data For Analogs

| Salt | MW | % remaining after 10 days Open to room conditions |
| --- | --- | --- |
| propane-1,3-bis(trimethylammonium) | 384.5 | 52 |
| 1-ethyl-3-methyl-1H-imidazolium | 446.5 | 75 |
| Trimethylphenylammonium | 496.6 | 85 |
| Tetrapropylammonium | 596.92 | *82 |
| Ammonium | 260.28 | *48 |
| Acetylcholine | 516.6 | 39 |
| Choline | 432.52 | 62 |
| Triethylphenylammonium | 580.77 | 76 |
| Methyltriethylammonium | 456.63 | 63 |
| 1,1-dimethylpyrrolidinium | 424.57 | 70 |
| butane-1,4-bis(trimethylammonium) | 398.53 | 40 |
| 1,4-dimethylpyridinium | 440.53 | 32 |
| Trimethylbenzylammonium | 524.69 | 94 |
| Ethylenebis(trimethylammonium) | 370.5 | 40 |
| pentane-1,5-bis(trimethylammonium) | 412.5 | 86 |
| bis(phenyltrimethylammonium) | 496.61 | 98 |
| bis(vinylmenthyammonium) | 396.49 | 72 |
| bis(cyclopropylmethyltrimethylammonium) | 452.60 | 86 |
| bis(benzylphenyldimethylammonium) | 648.81 | 45 |
| hexane-1,6-bis(trimethylammonium) | 426.56 | 94 |

* 9 days; different study
7 days, 74–77% RH, RT

6.28 Example 28

Biological Data Comparing Tetrathiomolybdate with Choline Tetrathiomolybdate In Vivo 3LL Lewis Lung Carcinoma: Primary Tumor Growth The tumor model used was 3LL JF in C57BL/6 mice. This tumor line arose spontaneously in 1951 as carcinoma of the lung in a C57BL/6 mouse (*Cancer Res.* 15:39, 1955. See, also Malave et al., *J. Nat'l. Canc. Inst.* 62:83–88 (1979). It is propagated by passage in C57BL/6 mice by subcutaneous inoculation and is tested in semiallogeneic C57BL/6× DBA/2 $F_1$ mice or in allogeneic C3H mice. Typically six animals per group for subcutaneously implant, or ten for intramuscular implant are used. Tumor may be implanted subcutaneously as a 2–4 mm fragment, or intramuscular or intramuscular as an inoculum of suspended cells of about 0.5–2×$10^6$-cells. Treatment begins 24 hours after implant or is delayed until a tumor of specified size (usually approximately 100 mg) can be palpated. The test compound is administered daily for 11–25 days.

Animals are followed by weighing, palpation and measurement of tumor size. Typical tumor weight in untreated control recipients on day 12 after subcutaneous inoculation is 500–2500 mg and typical median survival time is 18–28 days. A positive control compound, for example cyclophosphamide at 170 mg/kg/injection is given every 6 days. Results computed include mean animal weight, tumor size, tumor weight and survival time. For confirmed therapeutic activity, the test composition should be tested in two multidose assays. Female C57/BL mice were inoculated with 1×$10^6$ Lewis Lung carcinoma (3LL) cells subcutaneously in the middle of the back. Treatment with tetrathiomolybdate and choline thiomolybdate was initiated the day after tumor inoculation (50 mg/kg by gavage). Cyclophosphamide (170 mg/kg given every 6 days subcutaneously beginning on day 3 after tumor cell inoculation) was used as a control. Tumor volumes and animal weights were measured 2×/week and the animals euthanized when the volume of the tumors in the control group reached an average of 2000 mm$^3$. The ratio (T/C) of the tumor volumes in the treated group (T) to the control group (C) were determined. Terminal cardiac bleeds were obtained and analyzed for red blood cell concentration (hematocrit, HCT).

| TREATMENT | N | T/C | MOUSE WEIGHT % of initial | HCT** |
|---|---|---|---|---|
| Water | 19 | 1 | 106% | 35% |
| TM | 17 | 0.59 | 93%* | 35% |
| CHTM | 17 | 0.54 | 103% | 35% |
| Cyclophosphamide | 5 | 0.74 | 105% | 40% |

*significant; **normal is 45%

6.29 Example 29

Bis(choline) tetrathiomolybdate Inhibits the Proliferation of Endothelial Cells

Bis(choline) tetrathiomolybdate inhibits the proliferation of HUVECs in a dose dependent manner as illustrated in FIG. 1 and does not appear to be cytotoxic. Although exogenous copper was not added, the assay was performed in the presence of 10% serum. Serum contains proteins that bind copper and serum is approximately 1–2 µM with respect to copper content. Copper plays a role in the binding of bFGF to its receptor (Patstone et al., *J Biol. Chem.* 1996, 271(7):3343–6); accordingly bis(choline) tetrathiomolybdate may also have a direct impact on the mechanism of proliferation induction. Incubation of bis(choline) tetrathiomolybdate with confluent HUVECs (in a T-75) for 72 hours, and counting the cells directly at the end of the assay indicates that bis(choline) tetrathiomolybdate has little or no effect on confluent stable endothelial cells as can be seen from Table 1.

Effect of bis(choline) tetrathiomolybdate on viability of confluent HUVECs after 72 hours incubation at 37° C.

TABLE 1

| Conditions | cell number | viable cell number |
|---|---|---|
| 1. control | 390,000 | 335,000 |
| 2. control + 1 uM ATN-224 | 400,000 | 460,000 |
| 3. control + 10 uM ATN-224 | 535,000 | 555,000 |
| 4. control + 50 uM ATN-224 | 487,500 | 475,000 |

6.30 Example 30

Bis(choline) Tetrathiomolybdate Does Not Induce Apoptosis in Endothelial Cells

Figure 2:
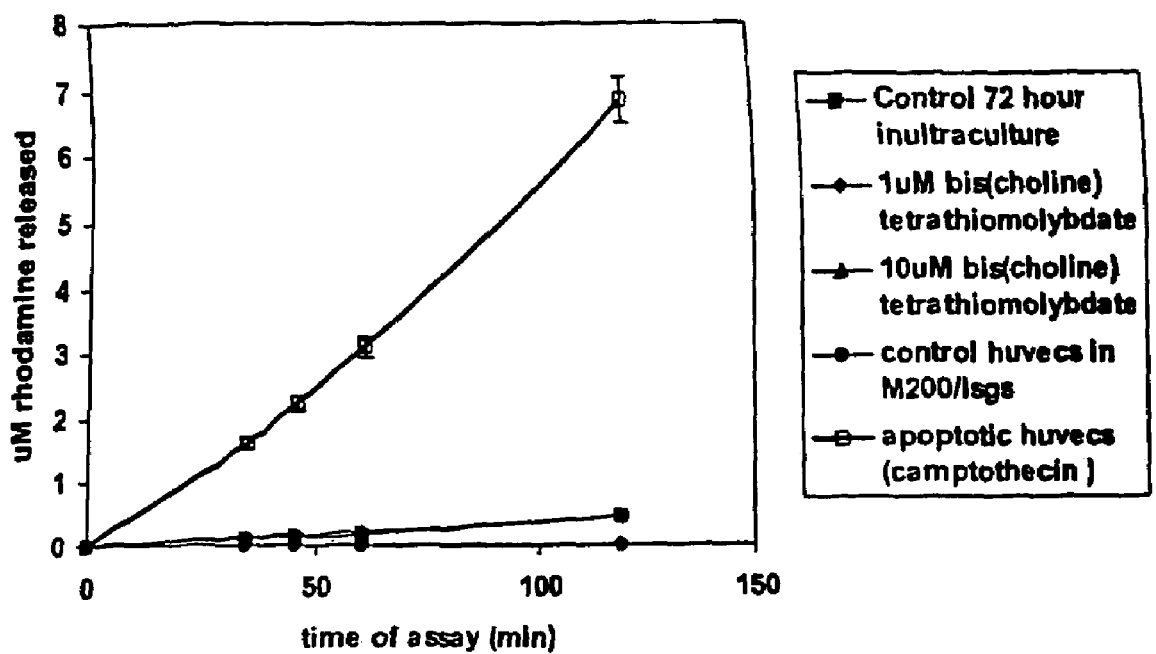
FIG. 2 illustrates that bis(choline) tetrathiomolybdate does not induce apoptosis in endothelial cells.

Endothelial cells were incubated with varying doses of bis(choline) tetrathiomolybdate for 72 hours (the time course of a typical proliferation assay) and the level of activated caspase-3 was measured. As can be seen from FIG. 2, incubation with bis(choline) tetrathiomolybdate does not lead to measurable levels of activated caspase-3 in endothelial cells. As a control, we incubated the same density of HUVECs with 10 µM camptothecin, a known inducer of apoptosis. Accordingly, HUVECs incubated with bis(choline) tetrathiomolybdate exhibit similar levels of activated caspase-3 as cells growing under normal proliferative conditions.

6.31 Example 31

Bis(choline) Tetrathiomolybdate is Anti-Angiogenic in a Matrigel Plug Assay

Figure 3:
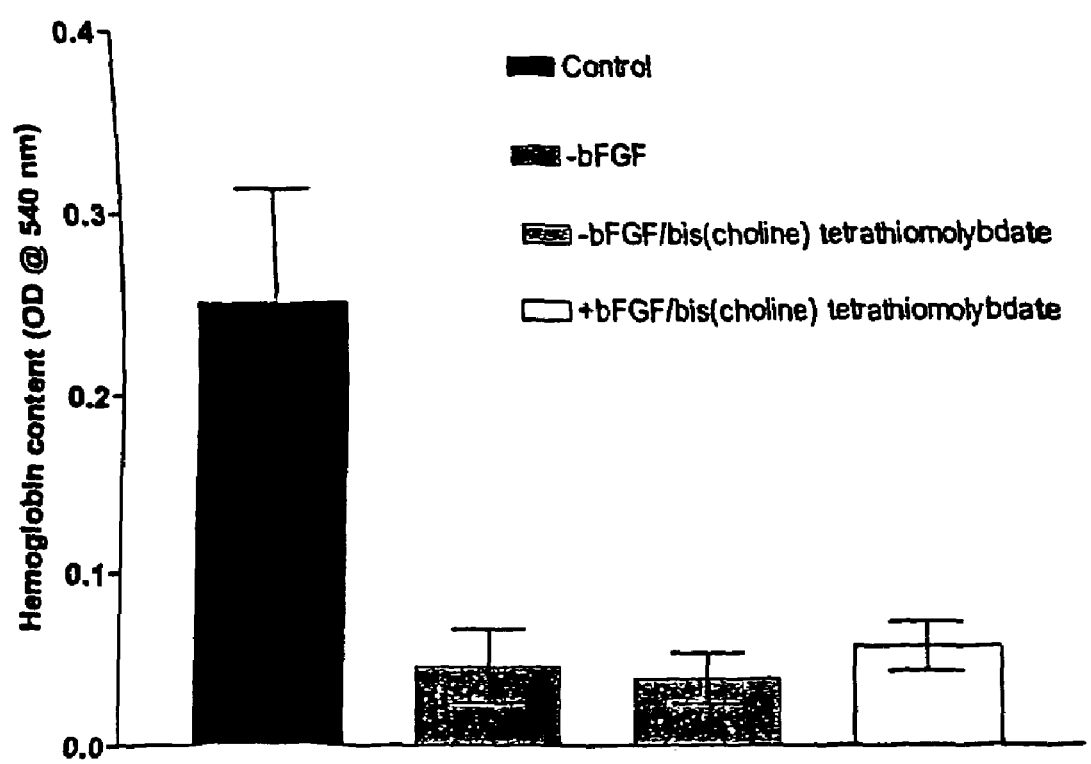
FIG. 3 illustrates that bis(choline) tetrathiomolybdate is anti-angiogenic in a matrigel plug assay.

The in vivo matrigel assay described in Example 35 is routinely used for measuring angiogenesis. Bis(choline) tetrathiomolybdate, administered orally by gavage, inhibits angiogenesis induced by bFGF in the in vivo matrigel assay, as illustrated in FIG. 3.

6.32 Example 32

Figure 4:
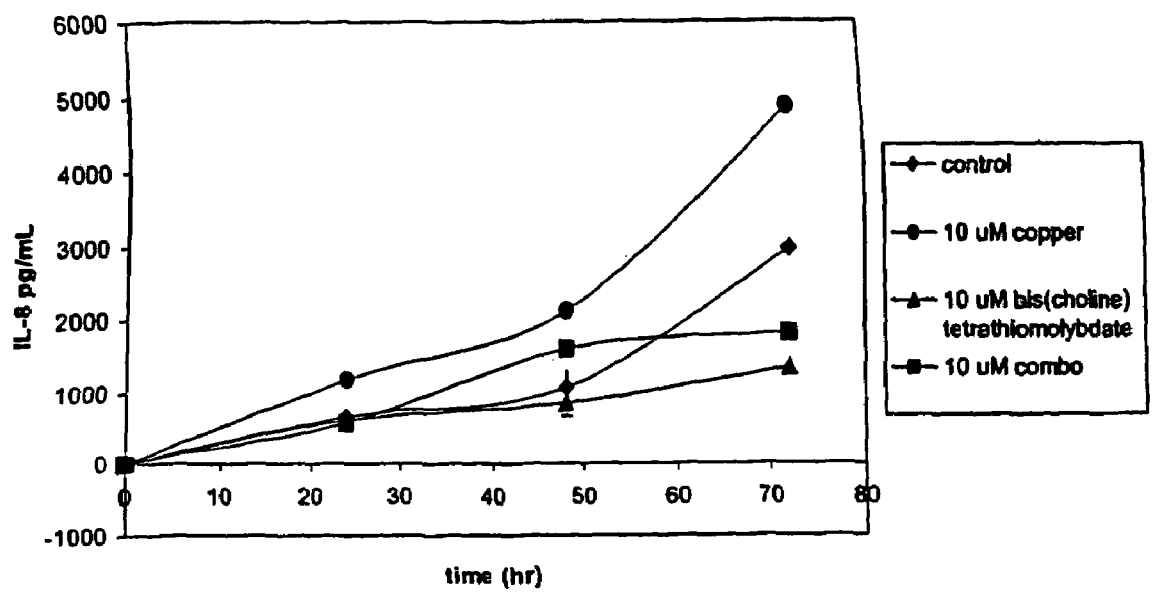
FIG. 4 illustrates that bis(choline) tetrathiomolybdate downregulates IL-8 secretion from confluent endothelial cells.

Bis(choline) Tetrathiomolybdate Downregulates IL-8 Secretion from Confluent Endothelial Cells As illustrated in FIG. 4, bis(choline) tetrathiomolybdate lowers the amount of IL-8 secreted from confluent endothelial cells. IL-8, as well as being a proangiogenic cytokine, is chemotactic for all known types of migratory immune cells.

6.33 Example 33

Figure 5:
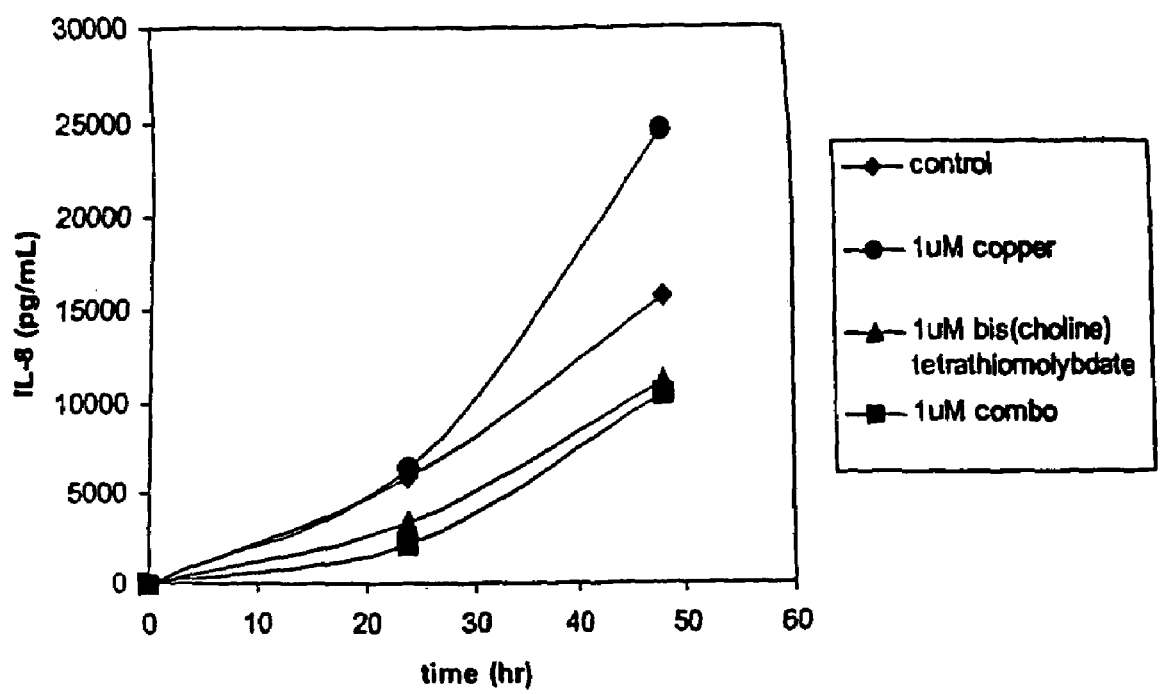
FIG. 5 illustrates that bis(choline) tetrathiomolybdate downregulates IL-8 expression from activated monocytes.

Bis(choline) Tetrathiomolybdate Downregulates IL-8 Expression from Activated Monocytes Unactivated monocytes do not express IL-8, but PMA activation of Thp-1 cells induces both IL-8 transcription and translation. FIG. 5 illustrates that bis(choline) tetrathiomolybdate is able to down regulate the expression/secretion of measurable IL-8 from activated monocytes.

6.34 Example 34

Bis(choline) Tetrathiomolybdate Causes a Decrease in Plasma Levels of Murine KC

Figure 6:
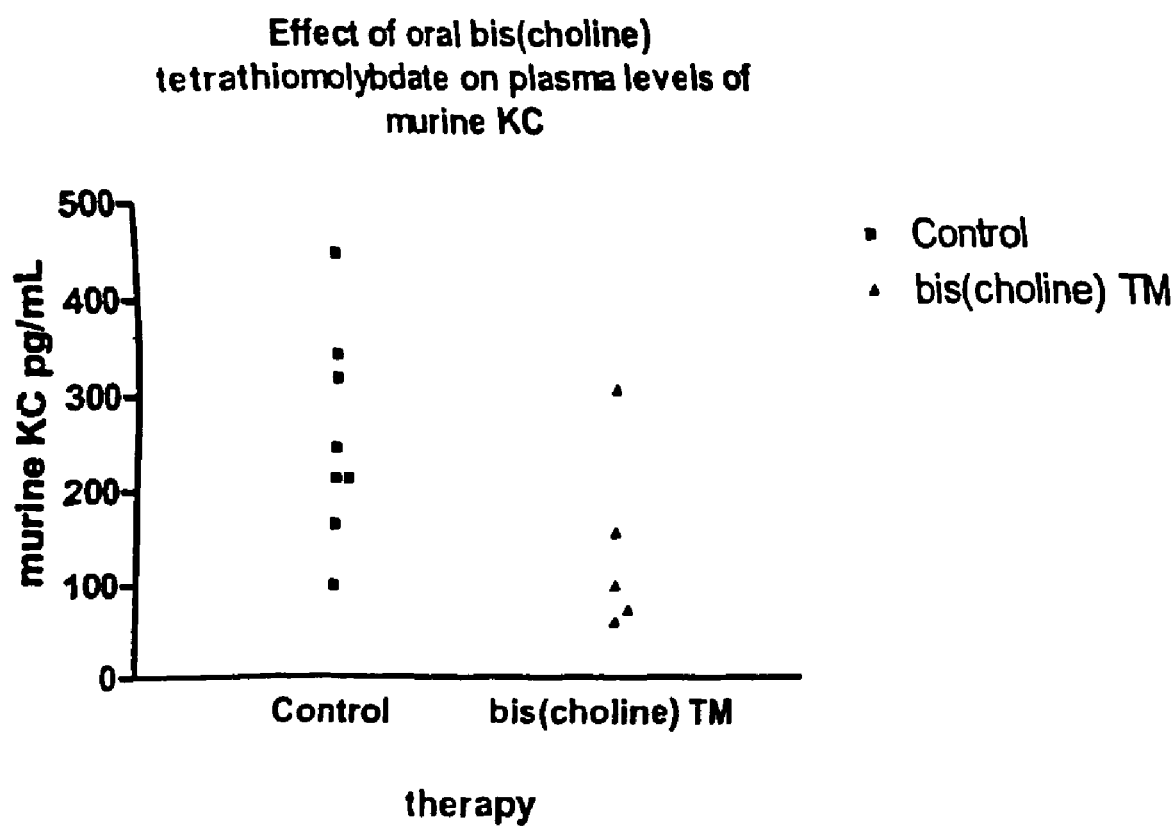
FIG. 6 illustrates that bis(choline) tetrathiomolybdate causes decrease in plasma levels of murine KC.

Mice do not express IL-8, but do express homologues, such as Murine KC. Murine KC actually has a higher homology to human GRO alpha than human IL-8, but its receptor has high homology to the human IL-8 receptor. The expression of murine KC is induced by TNF alpha. Bis(choline) tetrathiomolybdate was administered to tumor-bearing (Tumor-bearing mice have measurable murine KC in their plasma) C57/B16 mice (50 mg/kg daily) by gavage. Plasma samples were taken from the animals at day 21 of therapy and assayed for murine KC. Statistical analysis of these data indicated that there were significant (p<0. 1) differences between the mean murine KC values of the two groups as illustrated in FIG. 6.

6.35 Example 35

Matrigel Plug Assay

This assay is performed essentially as described by Passaniti et al., *Lab Invest.* 67:519–528 (1992). Ice-cold Matrigel® (e.g., 500 µL) (Collaborative Biomedical Products, Inc., Bedford, Mass.) is mixed with heparin (e.g., 50 µg/ml), FGF-2 (e.g., 400 ng/ml) and the compound to be tested. In some assays, bFGF may be substituted with tumor cells as the angiogenic stimulus. The Matrigel® mixture is injected subcutaneously into 4–8 week-old athymic nude mice at sites near the abdominal midline, preferably 3 injections per mouse. The injected Matrigel® forms a palpable solid gel. Injection sites are chosen such that each animal receives a positive control plug (such as FGF-2+ heparin), a negative control plug (e.g., buffer+heparin) and a plug that includes the compound being tested for its effect on angiogenesis, e.g., (FGF-2+ heparin+ compound). All treatments are preferably run in triplicate. Animals are sacrificed by cervical dislocation at about 7 days post injection or another time that may be optimal for observing angiogenesis. The mouse skin is detached along the abdominal midline, and the Matrigel® plugs are recovered and scanned immediately at high resolution. Plugs are then dispersed in water and incubated at 37° C. overnight. Hemoglobin levels are determined using Drabkin's solution (e.g., obtained from Sigma) according to the manufacturers' instructions. The amount of Hb in the plug is an indirect measure of angiogenesis as it reflects the amount of blood in the sample. In addition, or alternatively, animals may be injected prior to sacrifice with a 0.1 ml buffer (preferably PBS) containing a high molecular weight dextran to which is conjugated as a fluorophore. The amount of fluorescence in the dispersed plug, determined fluorimetrically, also serves as a measure of angiogenesis in the plug. Staining with mAb anti-CD31 (CD31 is "platelet-endothelial cell adhesion molecule or PECAM") may also be used to confirm neovessel formation and microvessel density in the plugs.

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims. All publications and patents cited herein are incorporated by reference.

What is claimed is:

1. A compound of structural formula (I):

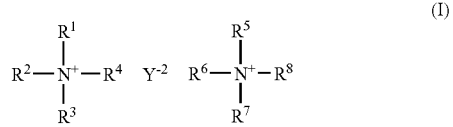

(I)

or a solvate or hydrate thereof wherein:
$R^1$, $R^2$, $R^3$, $R^5$, $R^6$ and $R^7$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, heteroalkyl or substituted heteroalkyl;

$R^4$ and $R^8$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, heteroalkyl or substituted heteroalkyl or are absent when N is part of an aromatic ring;

optionally, $R^1$ and $R^2$ taken together are alkyldiyl, substituted alkyldiyl, heteroalkyldiyl or substituted heteroalkyldiyl;

optionally, $R^5$ and $R^6$ taken together are alkyldiyl, substituted alkyldiyl, heteroalkyldiyl or substituted heteroalkyldiyl;

optionally, $R^1$ and $R^2$ taken together, $R^2$ and $R^3$ taken together and $R^2$ and $R^4$ taken together are alkyldiyl, substituted alkyldiyl, heteroalkyldiyl or substituted heteroalkyldiyl;

optionally, $R^5$ and $R^6$ taken together, $R^6$ and $R^7$ taken together and $R^6$ and $R^8$ taken together are alkyldiyl, substituted alkyldiyl, heteroalkyldiyl or substituted heteroalkyldiyl;

optionally, $R^3$ and $R^7$ taken together are alkyldiyl, substituted alkyldiyl, heteroalkyldiyl or substituted heteroalkyldiyl; and $Y^{-2}$ is $(Mo_2S_{12})^{-2}$, $(Mo_2S_9)^{-2}$, $(Mo_2S_7)^{-2}$, $(Mo_2S_8)^{-2}$, $(Mo_2S_{11})^{-2}$, $(Mo_2S_6)^{-2}$ or $(Mo_2S_{13})^{-2}$.

2. A compound of structural formula (I):

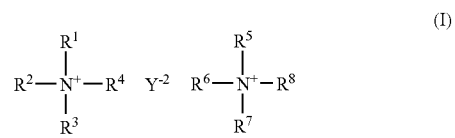

(I)

or a solvate or hydrate thereof wherein:
$R^2$, $R^3$, $R^5$, $R^6$ and $R^7$ are independently alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, heteroalkyl or substituted heteroalkyl;

$R^1$ is substituted alkyl, alkenyl, aryl, substituted aryl, arylalkyl, substituted arylalkyl, cycloalkyl, substituted cycloalkyl, cycloheteroalkyl, substituted cycloheteroalkyl, heteroaryl, heteroarylalkyl, substituted heteroarylalkyl, heteroalkyl or substituted heteroalkyl;

$R^4$ and $R^8$ are independently alkyl, substituted alkyl, aryl, substituted aryl, arylalkyl, substituted arylalkyl, cycloalkyl, substituted cycloalkyl, cycloheteroalkyl, substituted cycloheteroalkyl, heteroaryl, substituted heteroaryl, heteroarylalkyl, substituted heteroarylalkyl, heteroalkyl or substituted heteroalkyl or are absent when N is part of an aromatic ring;

optionally, $R^1$ and $R^2$ taken together are alkyldiyl, substituted alkyldiyl, heteroalkyldiyl or substituted heteroalkyldiyl;

optionally, $R^5$ and $R^6$ taken together are alkyldiyl, substituted alkyldiyl, heteroalkyldiyl or substituted heteroalkyldiyl;

optionally, $R^1$ and $R^2$ taken together, $R^2$ and $R^3$ taken together and $R^2$ and $R^4$ taken together are alkyldiyl, substituted alkyldiyl, heteroalkyldiyl or substituted heteroalkyldiyl;

optionally, $R^5$ and $R^6$ taken together, $R^6$ and $R^7$ taken together and $R^6$ and $R^8$ taken together are alkyldiyl, substituted alkyldiyl, heteroalkyldiyl or substituted heteroalkyldiyl;

wherein when N is part of an aromatic ring, the aromatic ring is imidazolium, pyrrolidinium or heteroalkyl substituted pyridinium; and $Y^{-2}$ is $(MoS_4)^{-2}$.

3. The compound of claim 1, wherein $$R^2-\overset{R^1}{\underset{R^3}{N^+}}-R^4 \quad = \quad R^6-\overset{R^5}{\underset{R^7}{N^+}}-R^8.$$

4. The compound of claim 2, wherein $$R^2-\overset{R^1}{\underset{R^3}{N^+}}-R^4 \quad = \quad R^6-\overset{R^5}{\underset{R^7}{N^+}}-R^8.$$

5. The compound of claim 1 or 3, wherein $R^1$, $R^2$ and $R^4$ are hydrogen, alkanyl or substituted alkanyl.

6. The compound of claim 1 or 3, wherein $R^1$, $R^2$ and $R^4$ are hydrogen, methyl or ethyl.

7. The compound of claim 1 or 3, wherein $R^1$ and $R^2$ are alkanyl.

8. The compound of claim 1 or 3, wherein $R^1$ and $R^2$ are methyl or ethyl.

9. The compound of claim 1 or 3, wherein $R^1$ is alkanyl, substituted alkanyl, alkenyl, substituted alkenyl, aryl, substituted aryl, arylalkyl, substituted arylalkyl, cycloalkyl or substituted cycloalkyl.

10. The compound of any one of claims 1–4, wherein $R^1$ and $R^2$ taken together are alkyleno, substituted alkyleno, heteroalkyleno or substituted heteroalkyleno.

11. The compound of any one of claims 1–4, wherein $R^1$ and $R^2$ taken together are alkyleno or heteroalkyleno.

12. The compound of any one of claims 1–4, wherein $R^1$ and $R^2$ taken together, $R^2$ and $R^3$ taken together and $R^2$ and $R^4$ taken together are alkyleno, substituted alkyleno, heteroalkyleno or substituted heteroalkyleno.

13. The compound of any one of claims 1–4, wherein $R^1$ and $R^2$ taken together, $R^2$ and $R^3$ taken together and $R^2$ and $R^4$ taken together are alkyleno.

14. The compound of any one of claims 1–4, wherein $R^1(R^2)(R^3)(R^4)N$ has the structure:

[structure depicted]

15. The compound of claim 1 or 3, wherein $R^3$ and $R^7$ taken together are alkyleno, substituted alkyleno, heteroalkyleno or substituted heteroalkyleno.

16. The compound of claim 1 or 3, wherein $R^3$ and $R^7$ taken together are alkyleno or heteroalkyleno.

17. The compound of claim 1 or 3, wherein $R^1$, $R^2$ and $R^4$ are hydrogen, alkanyl or substituted alkanyl and $R^3$ is substituted alkyl, aryl, arylalkyl, cycloalkyl or $R^3$ and $R^7$ taken together are alkyleno, substituted alkyleno, heteroalkyleno or substituted heteroalkyleno.

18. The compound of claim 1 or 3, wherein $R^1$, $R^2$ and $R^4$ are methyl or ethyl and $R^3$ is substituted alkyl, aryl, arylalkyl, cycloalkyl or $R^3$ and $R^7$ taken together are alkyleno or heteroalkyleno.

19. The compound of claim 1 or 3, wherein $R^1$, $R^2$ and $R^4$ are methyl or ethyl and $R^3$ is substituted alkyl, aryl, arylalkyl or cycloalkyl.

20. The compound of claim 1 or 3, wherein $R^1(R^2)(R^3)(R^4)N$ has the structure:

[structures depicted]

21. The compound of any one of claims 1–4, wherein $R^1(R^2)(R^3)(R^4)N$ has the structure:

[structure depicted]

22. The compound of claim 1 or 3, wherein $R^1(R^2)(R^3)(R^4)N$ has the structure:

[structure depicted]

23. The compound of claim 1 or 3, wherein $R^1$, $R^2$ and $R^4$ are methyl or ethyl and $R^3$ and $R^7$ taken together are alkyleno or heteroalkyleno.

24. The compound of any one of claims 1–4, wherein $R^1(R^2)(R^3)(R^4)N$ has the structure:

[structure depicted]

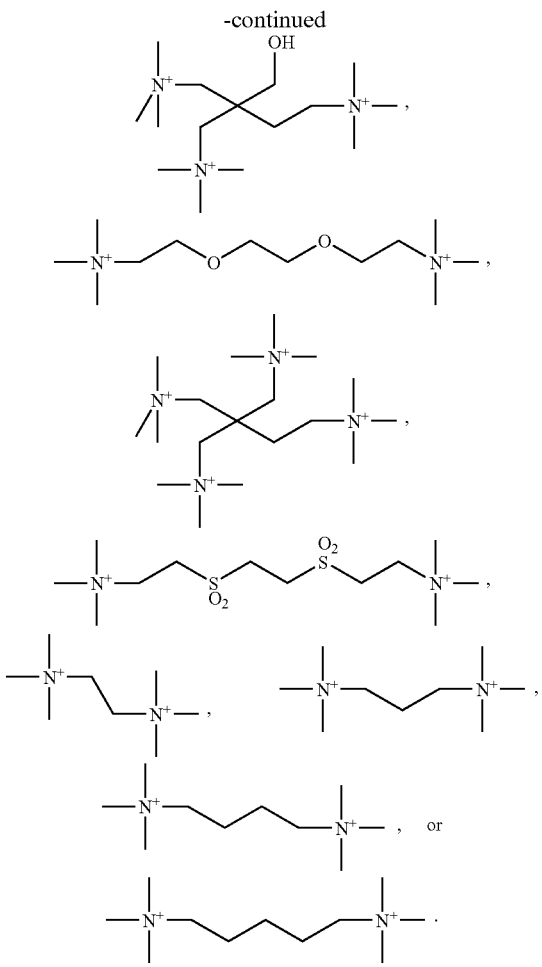

25. The compound of claim 1 or 3, wherein $R^1$, $R^2$ and $R^4$ are hydrogen and $R^3$ is substituted alkyl, cycloalkyl or substituted heteroaryl or $R^3$ and $R^7$ taken together are alkyleno.

26. The compound of claim 1 or 3, wherein $R^1$ and $R^2$ are alkanyl and $R^3$ and $R^4$ are hydrogen, alkyl, substituted alkyl, aryl, arylalkyl or alkyleno.

27. The compound of claim 1 or 3, wherein $R^1$ and $R^2$ are methyl or ethyl and $R^3$ and $R^4$ are hydrogen, alkyl, substituted alkyl, aryl, arylalkyl or alkyleno.

28. The compound of claim 1 or 3, wherein $R^1(R^2)(R^3)(R^4)N$ has the structure:

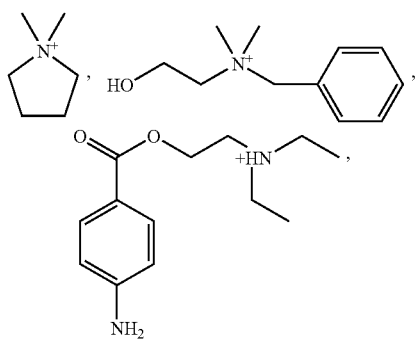

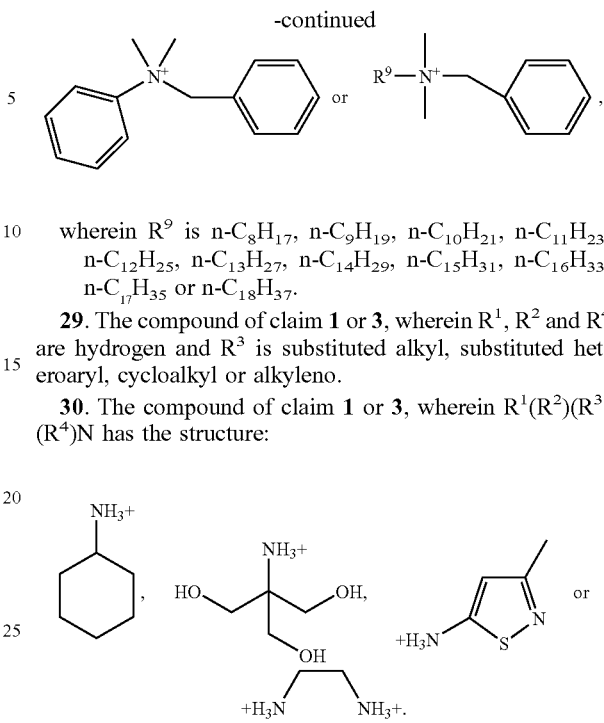

wherein $R^9$ is n-$C_8H_{17}$, n-$C_9H_{19}$, n-$C_{10}H_{21}$, n-$C_{11}H_{23}$, n-$C_{12}H_{25}$, n-$C_{13}H_{27}$, n-$C_{14}H_{29}$, n-$C_{15}H_{31}$, n-$C_{16}H_{33}$, n-$C_{17}H_{35}$ or n-$C_{18}H_{37}$.

29. The compound of claim 1 or 3, wherein $R^1$, $R^2$ and $R^4$ are hydrogen and $R^3$ is substituted alkyl, substituted heteroaryl, cycloalkyl or alkyleno.

30. The compound of claim 1 or 3, wherein $R^1(R^2)(R^3)(R^4)N$ has the structure:

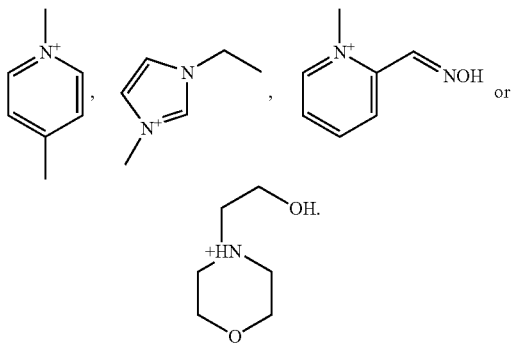

31. The compound of claim 1 or 3, wherein $R^1$ and $R^2$ taken together are alkyleno, substituted alkyleno, heteroalkyleno or substituted heteroalkyleno, $R^3$ is alkyl or substituted alkyl and $R^4$ is hydrogen or is absent.

32. The compound of claim 1 or 3, wherein $R^1(R^2)(R^3)N$ or $R^1(R^2)(R^3)(R^4)N$ has the structure:

33. A pharmaceutical composition comprising the compound of any one of claims 1–4 and a pharmaceutically acceptable diluent, excipient or adjuvant.

34. A method for treating cancer in a patient comprising administering to a patient in need of such treatment a therapeutically effective amount of the compound of any one of claims 1–4.

35. A method for treating cancer in a patient comprising administering to a patient in need of such treatment a therapeutically effective amount of the pharmaceutical composition of claim 33.

36. The method of claim 34 further comprising administering to the patient in need of such treatment a therapeutically effective amount of another anti-cancer agent or a pharmaceutical composition comprising i) said another anti-cancer agent and ii) a pharmaceutically acceptable diluent, excipient or adjuvant.

37. The method of claim 35 further comprising administering to the patient in need of such treatment a therapeutically effective amount of another anti-cancer agent or a pharmaceutical composition comprising i) said another anti-cancer agent and ii) a pharmaceutically acceptable diluent, excipient or adjuvant.

38. The method of claim 34 further comprising administering to the patient in need of such treatment a therapeutically effective amount of zinc or a pharmaceutical composition comprising i) zinc and ii) a pharmaceutically acceptable diluent, excipient or adjuvant.

39. The method of claim 35 further comprising administering to the patient in need of such treatment a therapeutically effective amount of zinc or a pharmaceutical composition comprising i) zinc and ii) a pharmaceutically acceptable diluent, excipient or adjuvant.

40. The method of claim 34, wherein the cancer is breast cancer, renal cancer, brain cancer, colon cancer, prostrate cancer, chondrosarcoma or angiosarcoma.

41. A method for treating wet type macular degeneration or rheumatoid arthritis in a patient comprising administering to a patient in need of such treatment a therapeutically effective amount of the compound of any one of claims 1–4.

42. A method for treating wet type macular degeneration or rheumatoid arthritis in a patient comprising administering to a patient in need of such treatment a therapeutically effective amount of the pharmaceutical composition of claim 33.

43. A method for treating aberrant vascularization in a patient comprising administering to a patient in need of such treatment a therapeutically effective amount of the compound of any one of claims 1–4.

44. A method for treating aberrant vascularization in a patient comprising administering to a patient in need of such treatment a therapeutically effective amount of the pharmaceutical composition of claim 33.

45. A method for treating excess copper levels in a patient comprising administering to a patient in need of such treatment a therapeutically effective amount of the compound of any one of claims 1–4.

46. A method for treating excess copper levels in a patient comprising administering to a patient in need of such treatment a therapeutically effective amount of the pharmaceutical composition of claim 33.

47. A method for treating obesity in a patient comprising administering to a patient in need of such treatment a therapeutically effective amount of the compound of any one of claims 1–4.

48. A method for treating obesity in a patient comprising administering to a patient in need of such treatment a therapeutically effective amount of the pharmaceutical composition of claim 33.

49. The method of claim 47 further comprising administering to the patient in need of such treatment a therapeutically effective amount of another anti-obesity agent or a pharmaceutical composition comprising i) said another anti-obesity agent and ii) a pharmaceutically acceptable diluent, excipient or adjuvant.

50. The method of claim 48 further comprising administering to the patient in need of such treatment a therapeutically effective amount of another anti-obesity agent or a pharmaceutical composition comprising i) said another anti-obesity agent and ii) a pharmaceutically acceptable diluent, excipient or adjuvant.

51. A method for treating neurodegenerative disease in a patient comprising administering to a patient in need of such treatment a therapeutically effective amount of the compound of any one of claims 1–4.

52. A method for treating neurodegenerative disease in a patient comprising administering to a patient in need of such treatment a therapeutically effective amount of the pharmaceutical composition of claim 33.

53. The method of claim 51, wherein the neurodegenerative disease is Alzheimer's disease, amyotrophic lateral sclerosis or prion disease.

54. The method of claim 52, wherein the neurodegenerative disease is Alzheimer's disease, amyotrophic lateral sclerosis or prion disease.

55. The method of claim 35, wherein the cancer is breast cancer, renal cancer, brain cancer colon cancer, prostrate cancer, chondrosarcoma or angiosarcoma.

56. The compound of claim 2 or 4, wherein $R^1(R^2)(R^3)(R^4)N$ has the structure:

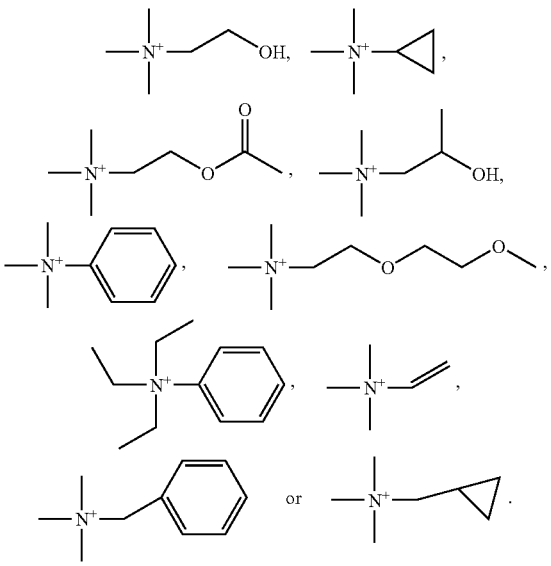

57. The compound of claim 2 or 4, wherein $R^1$ is substituted alkyl, aryl, arylalkyl or alkenyl, $R^2$ and $R^3$ are alkanyl, and $R^4$ is alkyl, substituted alkyl, aryl, arylalkyl or alkenyl.

58. The compound of claim 2 or 4, wherein $R^1$ is substituted alkyl, aryl, arylalkyl or alkenyl, $R^2$ and $R^3$ are methyl or ethyl, and $R^4$ is alkyl, substituted alkyl, aryl, arylalkyl or alkenyl.

59. A compound of structural formula (I):

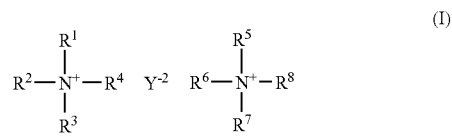

(I)

or a solvate or hydrate thereof wherein:
$R^1$, $R^2$, $R^4$, $R^5$, $R^6$ and $R^8$ are independently hydrogen, alkyl, substituted alkyl, or aryl;
$R^3$ and $R^7$ taken together are alkyldiyl, substituted alkyldiyl, heteroalkyldiyl or substituted heteroalkydiyl; and
$Y^{-2}$ is $(MoS_4)^{-2}$.

60. A compound of structural formula (I):

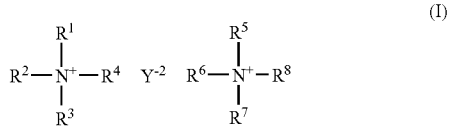

or a solvate or hydrate thereof wherein:
$R^1$, $R^2$ and $R^4$ are independently ethyl, propyl or butyl;
$R^3$, $R^5$, $R^6$, $R^7$ and $R^8$ are independently alkyl; and
$Y^{-2}$ is $(MoS_4)^{-2}$.

61. The compound of claim 60, wherein $R^1(R^2)(R^3)(R^4)N$ has the structure:

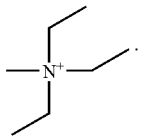

62. A compound of structural formula (I):

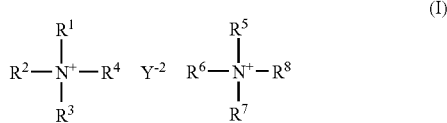

or a solvate or hydrate thereof wherein:
$R^1$ and $R^5$ are benzyl;
$R^2$, $R^3$, $R^4$, $R^6$, $R^7$ and $R^8$ are independently methyl and;
$Y^{-2}$ is $(MoS_4)^{-2}$.

63. A compound of structural formula (I):

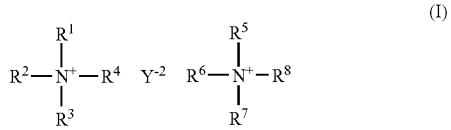

or a solvate or hydrate thereof wherein:
$R^1$ and $R^5$ are 2-hydroxyethyl;
$R^2$, $R^3$, $R^4$, $R^6$, $R^7$ and $R^8$ are independently methyl and;
$Y^{-2}$ is $(MoS_4)^{-2}$.

64. A pharmaceutical composition comprising i) the compound of claim 62 or 63 and ii) a pharmaceutically acceptable diluent, excipient or adjuvant.

65. A method for treating cancer in a patient comprising administering to a patient in need of such treatment a therapeutically effective amount of the compound of claim 62 or 63.

66. A method for treating cancer in a patient comprising administering to a patient in need of such treatment a therapeutically effective amount of the pharmaceutical composition of claim 64.

67. The method of claim 65 further comprising administering to the patient in need of such treatment a therapeutically effective amount of another anti-cancer agent or a pharmaceutical composition comprising i) said another anti-cancer agent and ii) a pharmaceutically acceptable diluent, excipient or adjuvant.

68. The method of claim 66 further comprising administering to the patient in need of such treatment a therapeutically effective amount of another anti-cancer agent or a pharmaceutical composition comprising i) said another anti-cancer agent and ii) a pharmaceutically acceptable diluent, excipient or adjuvant.

69. The method of claim 65 further comprising administering to a patient in need of such treatment a therapeutically effective amount of zinc or a pharmaceutical composition comprising i) zinc and ii) a pharmaceutically acceptable diluent, excipient or adjuvant.

70. The method of claim 66 further comprising administering to a patient in need of such treatment a therapeutically effective amount of zinc or a pharmaceutical composition comprising i) zinc and ii) a pharmaceutically acceptable diluent, excipient or adjuvant.

71. The method of claim 65, wherein the cancer is breast cancer, renal cancer, brain cancer, colon cancer, prostrate cancer, chondrosarcoma or angiosarcoma.

72. The method of claim 66, wherein the cancer is breast cancer, renal cancer, brain cancer, colon cancer, prostrate cancer, chondrosarcoma or angiosarcoma.

73. A method for treating wet type macular degeneration or rheumatoid arthritis in a patient comprising administering to a patient in need of such treatment a therapeutically effective amount of the compound of claim 62 or 63.

74. A method for treating wet type macular degeneration or rheumatoid arthritis in a patient comprising administering to a patient in need of such treatment a therapeutically effective amount of the pharmaceutical composition of claim 64.

75. A method for treating aberrant vascularization in a patient comprising administering to a patient in need of such treatment a therapeutically effective amount of the compound of claim 62 or 63.

76. A method for treating aberrant vascularization in a patient comprising administering to a patient in need of such treatment a therapeutically effective amount of the pharmaceutical composition of claim 64.

77. A method for treating excess copper levels in a patient comprising administering to a patient in need of such treatment a therapeutically effective amount of the compound of claim 62 or 63.

78. A method for treating excess copper levels in a patient comprising administering to a patient in need of such treatment a therapeutically effective amount of the pharmaceutical composition of claim 64.

79. A method for treating obesity in a patient comprising administering to a patient in need of such treatment a therapeutically effective amount of the compound of claim 62 or 63.

80. A method for treating obesity in a patient comprising administering to a patient in need of such treatment a therapeutically effective amount of the pharmaceutical composition of claim 64.

81. The method of claim 79 further comprising administering to the patient in need of such treatment a therapeutically effective amount of another anti-obesity agent or a pharmaceutical composition comprising i) said another anti-obesity agent and ii) a pharmaceutically acceptable diluent, excipient or adjuvant.

82. The method of claim 80 further comprising administering to the patient in need of such treatment a therapeutically effective amount of another anti-obesity agent or a pharmaceutical composition comprising i) said another anti-obesity agent and ii) a pharmaceutically acceptable diluent, excipient or adjuvant.

83. A method for treating neurodegenerative disease in a patient comprising administering to a patient in need of such treatment a therapeutically effective amount of the compound of claim 62 or 63.

84. A method for treating neurodegenerative disease in a patient comprising administering to a patient in need of such treatment a therapeutically effective amount of the pharmaceutical composition of claim 64.

85. The method of claim 83, wherein the neurodegenerative disease is Alzheimer's disease, amyotrophic lateral sclerosis or prion disease.

86. The method of claim 84, wherein the neurodegenerative disease is Alzheimer's disease, amyotrophic lateral sclerosis or prion disease.

87. A compound of structural formula (I):

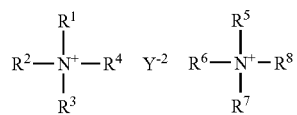

or a solvate or hydrate thereof wherein:
$Y^{-2}$ is $(MoS_4)^{-2}$;
$R^1(R^2)(R^3)(R^4)N=R^5(R^6)(R^7)(R^8)N$; and
$R^1(R^2)(R^3)(R^4)N$ has the structure:

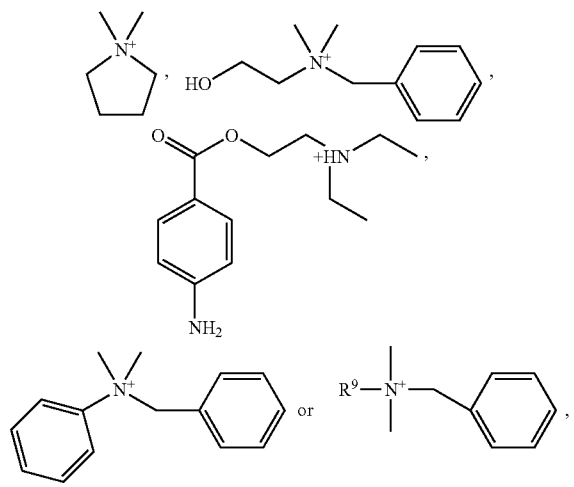

wherein $R^9$ is n-$C_8H_{17}$, n-$C_9H_{19}$, n-$C_{10}H_{21}$, n-$C_{11}H_{23}$, n-$C_{12}H_{25}$, n-$C_{13}H_{27}$, n-$C_{14}H_{29}$, n-$C_{15}H_{31}$, n-$C_{16}H_{33}$, n-$C_{17}H_{35}$ or n-$C_{18}H_{37}$.

88. A compound of structural formula (I):

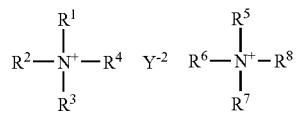

or a solvate or hydrate thereof wherein:
$Y^{-2}$ is $(MoS_4)^{-2}$;
$R^1(R^2)(R^3)(R^4)N=R^5(R^6)(R^7)(R^8)N$; and wherein $R^1(R^2)(R^3)(R^4)N$ has the structure:

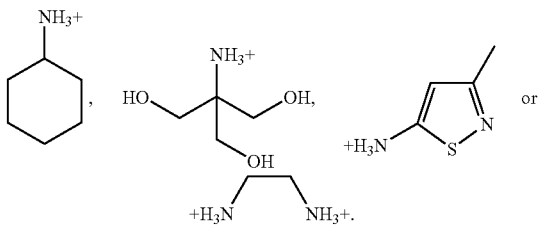

89. A compound of structural formula (I):

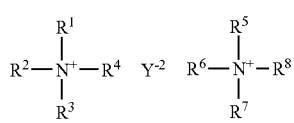

or a solvate or hydrate thereof wherein:
$Y^{-2}$ is $(MoS_4)^{-2}$; wherein
a) $R^1(R^2)(R^3)N=R^5(R^6)(R^7)N$; and $R^1(R^2)(R^3)N$ has the structure:

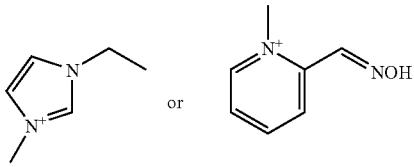

or
b) $R^1(R^2)(R^3)(R^4)N=R^5(R^6)(R^7)(R^8)N$; and $R^1(R^2)(R^3)(R^4)N$ has the structure:

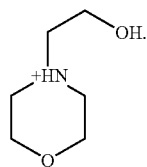

90. The method of claim 34 wherein the patient is human.
91. The method of claim 35 wherein the patient is human.
92. The method of claim 41 wherein the patient is human.
93. The method of claim 42 wherein the patient is human.
94. The method of claim 43 wherein the patient is human.
95. The method of claim 44 wherein the patient is human.
96. The method of claim 45 wherein the patient is human.
97. The method of claim 46 wherein the patient is human.
98. The method of claim 47 wherein the patient is human.
99. The method of claim 51 wherein the patient is human.
100. The method of claim 52 wherein the patient is human.
101. The method of claim 65 wherein the patient is human.
102. The method of claim 66 wherein the patient is human.
103. The method of claim 73 wherein the patient is human.

104. The method of claim 74 wherein the patient is human.

105. The method of claim 75 wherein the patient is human.

106. The method of claim 76 wherein the patient is human.

107. The method of claim 77 wherein the patient is human.

108. The method of claim 78 wherein the patient is human.

109. The method of claim 79 wherein the patient is human.

110. The method of claim 80 wherein the patient is human.

111. The method of claim 83 wherein the patient is human.

112. The method of claim 84 wherein the patient is human.

* * * * *